US008326582B2

(12) United States Patent
Mian et al.

(10) Patent No.: US 8,326,582 B2
(45) Date of Patent: Dec. 4, 2012

(54) ACOUSTIC-BASED ROTATING COMPONENT ANALYSIS

(75) Inventors: Zahid F. Mian, Loudonville, NY (US); Richard L. Smith, Clifton Park, NY (US)

(73) Assignee: International Electronic Machines Corporation, Troy, NY (US)

( * ) Notice: Subject to any disclaimer, the term of this patent is extended or adjusted under 35 U.S.C. 154(b) by 412 days.

(21) Appl. No.: 12/642,025

(22) Filed: Dec. 18, 2009

(65) Prior Publication Data

US 2010/0161255 A1    Jun. 24, 2010

Related U.S. Application Data

(60) Provisional application No. 61/193,713, filed on Dec. 18, 2008.

(51) Int. Cl.
*G01N 29/04* (2006.01)

(52) U.S. Cl. ............. 702/190; 702/99; 702/56; 367/99; 367/98; 367/124; 367/131; 340/682; 340/540; 73/489; 73/660

(58) Field of Classification Search ............... 702/99, 702/190, 56; 367/99, 98, 124, 131; 340/682, 340/540; 73/489, 660
See application file for complete search history.

(56) References Cited

U.S. PATENT DOCUMENTS

| | | | |
|---|---|---|---|
| 4,550,603 A | 11/1985 | Fukada et al. | |
| 4,550,604 A | 11/1985 | Sugimoto et al. | |
| 4,790,190 A | 12/1988 | Bambara et al. | |
| 4,843,885 A | 7/1989 | Bambara | |
| 5,029,477 A * | 7/1991 | Bambara | 73/660 |
| 5,150,618 A | 9/1992 | Bambara | |
| 5,386,372 A * | 1/1995 | Kobayashi et al. | 700/280 |
| 5,435,184 A * | 7/1995 | Pineroli et al. | 73/489 |
| 5,471,434 A * | 11/1995 | Davis et al. | 367/124 |
| 5,619,616 A * | 4/1997 | Brady et al. | 706/20 |
| 5,804,726 A | 9/1998 | Geib et al. | |
| 5,877,948 A * | 3/1999 | Dijkmans | 363/60 |
| 5,877,998 A * | 3/1999 | Aidala et al. | 367/124 |
| 6,370,957 B1 * | 4/2002 | Filippenko et al. | 73/660 |
| 6,377,876 B1 | 4/2002 | Hedeen et al. | |
| 6,507,790 B1 | 1/2003 | Radomski | |
| 6,772,633 B2 | 8/2004 | Terry et al. | |
| 6,951,132 B2 | 10/2005 | Davenport et al. | |
| 6,985,803 B2 | 1/2006 | Abdel-Malek et al. | |

(Continued)

OTHER PUBLICATIONS

Brotherhood of Locomotive Engineers and Trainmen, A division of the Rail Conference of the International Brotherhood of Teamsters, "CPR Installs "Smart" Sound Technology for Predicting Wheel Bearing Failure", CPR Issued the News Release on Dec. 6, 2004, pp. 1-2.

(Continued)

*Primary Examiner* — Carol Tsai
(74) *Attorney, Agent, or Firm* — Hoffman Warnick LLC

(57) ABSTRACT

An acoustic sensor acquires acoustic data corresponding to a rotating component of a machine during operation of the machine. The acoustic sensor can be configured to enhance acoustic signals in a range of frequencies corresponding to at least one evaluated condition of the rotating component and/or enhance the acoustic signals received from a directional area narrowly focused on the rotating component. The rotating component is evaluated using the acoustic data acquired by the acoustic sensor. In an embodiment, the machine can be a vehicle traveling past a parabolic microphone. In a more specific embodiment, the vehicle is a rail vehicle and the rotating component is a railroad wheel bearing.

20 Claims, 12 Drawing Sheets

U.S. PATENT DOCUMENTS

| | | | |
|---|---|---|---|
| 6,990,419 | B2 | 1/2006 | Ramillon et al. |
| 7,027,953 | B2 | 4/2006 | Klein |
| 7,103,460 | B1 | 9/2006 | Breed |
| 7,184,930 | B2 | 2/2007 | Miyasaka et al. |
| 7,187,773 | B2 | 3/2007 | Hamada et al. |
| 7,213,789 | B1 | 5/2007 | Matzan |
| 7,239,239 | B2 * | 7/2007 | Dobler et al. ............... 340/540 |
| 7,260,022 | B2 * | 8/2007 | Schliep et al. ............... 367/124 |
| 7,355,508 | B2 | 4/2008 | Mian et al. |
| 7,437,274 | B2 | 10/2008 | Charette et al. |
| 7,587,299 | B2 | 9/2009 | Miyasaka et al. |
| 7,602,937 | B2 | 10/2009 | Mian et al. |
| 7,693,673 | B2 * | 4/2010 | Luo et al. ............... 702/99 |
| 7,705,743 | B2 * | 4/2010 | Barone et al. ............... 340/682 |
| 2007/0118333 | A1 | 5/2007 | Miyasaka et al. |
| 2007/0208841 | A1 * | 9/2007 | Barone et al. ............... 709/223 |
| 2008/0134789 | A1 | 6/2008 | Schneider et al. |
| 2008/0306705 | A1 | 12/2008 | Luo et al. |
| 2009/0001226 | A1 | 1/2009 | Haygood |
| 2009/0018721 | A1 | 1/2009 | Mian et al. |
| 2009/0055041 | A1 | 2/2009 | Mian et al. |
| 2009/0055043 | A1 | 2/2009 | Mian et al. |

OTHER PUBLICATIONS

Bladon et al., "Predictive Condition Monitoring of Railway Rolling Stock", Conference on Railway Engineering, Darwin Jun. 20-23, 2004.

Southern et al., "RailBAM®—An Advanced Bearing Acoustic Monitor: Initial Operational Performance Results", Conference on Railway Engineering, Darwin Jun. 20-23, 2004, pp. 1-7.

Transit Cooperative Research Program, TCRP Report 71, "Track-Related Research: vol. 1", Control of Wheel/Rail Friction, Transportation Research Board—National Research Council, National Academy Press, Washington, D.C., pp. 42-70, 2001.

Transit Cooperative Research Program, "Research Results Digest 76", Responsible Senior Program Officer: Christopher W. Jenks, Feb. 2006, pp. 1-7.

Anderson et al., "Acoustic Detection of Rail Car Roller Bearing Defects: Phase III, System Evaluation Test", U.S. Department of Transportation, Final Report, Aug. 2003, 49 pages.

Anderson et al., "Acoustic Detection of Roller Bearing Defects: Phase II, Field Test", U.S. Department of Transportation, Final Report, Aug. 2003, 60 pages.

Smith et al., "Railcar Bearing End-Life Failure Distances on the Canadian and United States Railroads", The Winter Annual Meeting of the American Society of Mechanical Engineers, San Francisco, California, Dec. 10-15, 1989, pp. 45-50.

Smith et al., "Railcar Bearing End-Life Failure Distances and Acoustical Defect Censuring Methods", The Winter Annual Meeting, Chicago, Illinois, Nov. 27-Dec. 2, 1988, pp. 1-7.

Richard Smith, "Innovative Sound Processing Techniques for Secure Product Maintenance", The $2^{nd}$ Annual Tech Valley Symposium, Apr. 18, 2006, Albany, New York, pp. 1-18.

* cited by examiner

ACOUSTIC-BASED ROTATING COMPONENT ANALYSIS

REFERENCE TO PRIOR APPLICATION

The current application claims the benefit of co-pending U.S. Provisional Application No. 61/193,713, titled "System and method for acoustic evaluation of rotating components", which was filed on 18 Dec. 2008, and which is hereby incorporated by reference.

TECHNICAL FIELD

The disclosure relates generally to the evaluation of rotating components, and more particularly, to evaluating rotating components using acoustic data.

BACKGROUND ART

In the United States, a rolling element bearing burns off from a rail vehicle axle an average of approximately once per week. Many of these incidents result in catastrophic accidents and extensive rail traffic disruption. Other incidents are relatively minor, however, still can temporarily slow or halt rail traffic, resulting in disruption of product delivery. Ultimately, failing bearings can cost many thousands to many millions of dollars for each incident in the rail industry.

Similarly, failure of a wheel bearing on a commercial truck or bus can result in fire or loss of a wheel with significant effects on public safety. Considerable safety and financial value also can be found in the early detection of flaws in bearings for drive shafts for gas turbine engines employed in jet aircraft, electrical power plants, and other industrial operations.

The rail industry has utilized hotbox detectors for an extended period of time to detect overheating bearings and thereby prevent incidents, such as derailment. Each detector includes an infrared sensor that measures the heat associated with a wheel as it passes, and is mounted on the rail or in close proximity to the rail to provide hot wheel data. Unfortunately, hotbox detectors only detect the heat from a bearing that is already well into failure. Some estimates suggest that once a hotbox detector detects a hot bearing, the rail wheel may have only a few miles left before the bearing burns off. To this extent, hotbox detectors are often installed only miles apart along a line to ensure detection prior to an incident occurring.

Regardless, the warning provided by a hotbox detector is often too late to prevent the failure. As a result, whenever a hotbox detector gives an alarm, a train is typically stopped, the bearing physically examined by an engineer, and, if the bearing is indeed hot, the train proceeds at a very low speed (e.g., approximately 2-3 mph) to the nearest siding or spur, where a trackside repair can be carried out. As the nearest siding or spur may be many miles away, this can result in many hours of delay, not just for the affected train, but any other trains traveling on the same line.

Alternative approaches seek to detect faults in rotating components of machinery using vibration data. In these approaches, signal analysis can be applied to the vibration data to determine the presence of a fault. However, these approaches require that the vibration data be acquired by one or more sensors attached to the monitored equipment, which transmits the vibration data to a processing system. Such a configuration is not always desired or possible.

Research has been conducted into the use of acoustic data for evaluating bad wheel bearings. Such research has provided evidence that acoustic data can be used to detect internal roller bearing faults at large standoff distances from operating bearings. In the rail industry, defective railcar roller bearings on freight cars have been detected using acoustic wayside monitoring equipment regardless of whether the freight cars are empty or fully loaded. One approach proposes to use horn-based band pass units and electret microphones as well as the extraction of a signal envelope for use with a hardware band pass filter for the detection of specific frequencies in the acoustic data. Additionally, the use of wheel detectors to determine a likely window within which bearing sounds are expected has been proposed.

In a commercially implemented approach, a twelve microphone array wayside system is used to perform acoustic detection. In this approach, the microphones are spaced approximately three feet apart and each is installed approximately three feet from the rail. To this extent, the system requires a significant amount of data processing (e.g., acoustic data from the twelve microphones) and a significant length of rail (e.g., approximately thirty-two feet). Additionally, the microphones are installed within the distance normally allowed for permanently installed devices, and too close for actual protection of the equipment. As a result, the equipment is frequently damaged by passing trains. Still another approach uses arrays of standard microphones to identify and assess bearing faults. However, this approach also requires that the arrays be placed fairly close to the track, requires multiple passes to detect faulty bearings, and requires installation at every monitored track.

One reason for using multiple linear arrays of microphones to monitor moving objects is to observe the object for a longer period of time. Time slicing of the moving object sound source then can be used to provide an extensive period of recording from the center of the moving object. For faulty railroad bearing detection, it is typically assumed that data for at least two or three revolutions is required to optimize the fault detection signature. As a result, it is argued that the more rotations that are observed, the resulting diagnostic signal will be more accurate. To this extent, it has been noted that the use of a parabolic reflector microphone limits the acoustic capturing arc (e.g., the portion of space in which a given passing signal will be detected by the microphone), which can reduce the effective acoustic bearing scan time.

SUMMARY OF THE INVENTION

An embodiment of the invention enables early warning of a failing component of rotating equipment, such as a bearing of a vehicle wheel, a machinery shaft, or the like, based on acoustic data acquired while the component is in operation. For example, a more particular embodiment of the invention can detect a failing bearing on a rail vehicle tens of thousands of miles before complete failure occurs. Other embodiments of the invention can be configured to detect worn bearings on other types of moving wheeled vehicles, such as commercial trucks and buses. Furthermore, other flaws of rotating components with distinguishable acoustic characteristics can be detected.

Aspects of the invention provide a solution in which an acoustic sensor acquires acoustic data corresponding to a rotating component of a machine during operation of the machine. The acoustic sensor can be configured to enhance acoustic signals in a range of frequencies corresponding to at least one evaluated condition of the rotating component and/or enhance the acoustic signals received from a directional area narrowly focused on the rotating component. The rotating component is evaluated using the acoustic data acquired by the acoustic sensor. In an embodiment, the machine can be a vehicle traveling past a parabolic microphone. In a more specific embodiment, the vehicle is a rail vehicle and the rotating component is a railroad wheel bearing.

A first aspect of the invention provides a system comprising: an acoustic sensor configured to acquire acoustic data corresponding to a rotating component of a machine during operation of the machine, wherein the acoustic sensor is configured to enhance acoustic signals in a range of frequencies corresponding to at least one evaluated condition of the rotating component and enhance the acoustic signals received from a directional area narrowly focused on the rotating component; and a computer system including at least one computing device configured to evaluate the rotating component by: obtaining the acoustic data corresponding to the rotating component; determining whether any one of the at least one evaluated condition is present in the rotating component based on the acoustic data corresponding to the rotating component; and storing a result of the determining.

A second aspect of the invention provides a system comprising: an acoustic sensor configured to acquire acoustic data received from a fixed narrowly focused directional area, wherein the directional area includes a target area through which a rotating component of a vehicle moves during operation of the vehicle; and a computer system including at least one computing device configured to evaluate the rotating component by: obtaining acoustic data corresponding to the rotating component as the rotating component moved through the target area; determining whether any one of at least one evaluated condition is present in the rotating component based on the acoustic data corresponding to the rotating component, the determining including: extracting a set of features from the acoustic data corresponding to the rotating component and analyzing the set of features for at least one condition feature associated with the at least one evaluated condition.

A third aspect of the invention provides a system comprising: an acoustic sensor configured to acquire acoustic data received from a fixed narrowly focused directional area, wherein the directional area includes a target area through which a rotating component of a rail vehicle moves during operation of the rail vehicle, and wherein the acoustic sensor is configured to enhance acoustic signals in a range of frequencies corresponding to at least one evaluated condition of the rotating component and enhance the acoustic signals received from a directional area narrowly focused on the rotating component; and a computer system including at least one computing device configured to evaluate the rotating component by: obtaining acoustic data corresponding to the rotating component as the rotating component moved through the target area; determining whether any one of at least one evaluated condition is present in the rotating component based on the acoustic data corresponding to the rotating component, the determining including: extracting a set of features from the acoustic data corresponding to the rotating component and analyzing the set of features for at least one condition feature associated with the at least one evaluated condition.

A fourth aspect of the invention provides a method for evaluating a rotating component, the method comprising: obtaining acoustic data corresponding to the rotating component of a machine during operation of the machine, wherein the acoustic data includes enhanced acoustic signals in a range of frequencies corresponding to at least one evaluated condition of the rotating component and enhanced acoustic signals received from a directional area narrowly focused on the rotating component; determining whether any one of the at least one evaluated condition is present in the rotating component based on the acoustic data corresponding to the rotating component; and storing a result of the determining.

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution in which an acoustic sensor acquires acoustic data corresponding to a rotating component of a machine during operation of the machine. The acoustic sensor can be configured to enhance acoustic signals in a range of frequencies corresponding to at least one evaluated condition of the rotating component and/or enhance the acoustic signals received from a directional area narrowly focused on the rotating component. The rotating component is evaluated using the acoustic data acquired by the acoustic sensor. In an embodiment, the machine can be a vehicle traveling past a parabolic microphone. In a more specific embodiment, the vehicle is a rail vehicle and the rotating component is a railroad wheel bearing. As used herein, unless otherwise noted, the term "set" means one or more (i.e., at least one) and the phrase "any solution" means any now known or later developed solution.

In general, an embodiment of the invention acquires data, including data relating to acoustic signals, corresponding to a target rotating component for evaluation. An embodiment of the invention also acquires other data, which permits the extraction of data relating to the target rotating component's acoustic signals from data relating to background noise. The data corresponding to the acoustic signals of the target rotating component is analyzed to determine the presence of one or more conditions, the nature of one or more conditions, a response to a detected condition, and/or the like. In this manner, embodiments of the invention enable the evaluation of one or more target rotating components from a standoff distance without requiring any physical connection to the component.

Figure 1:
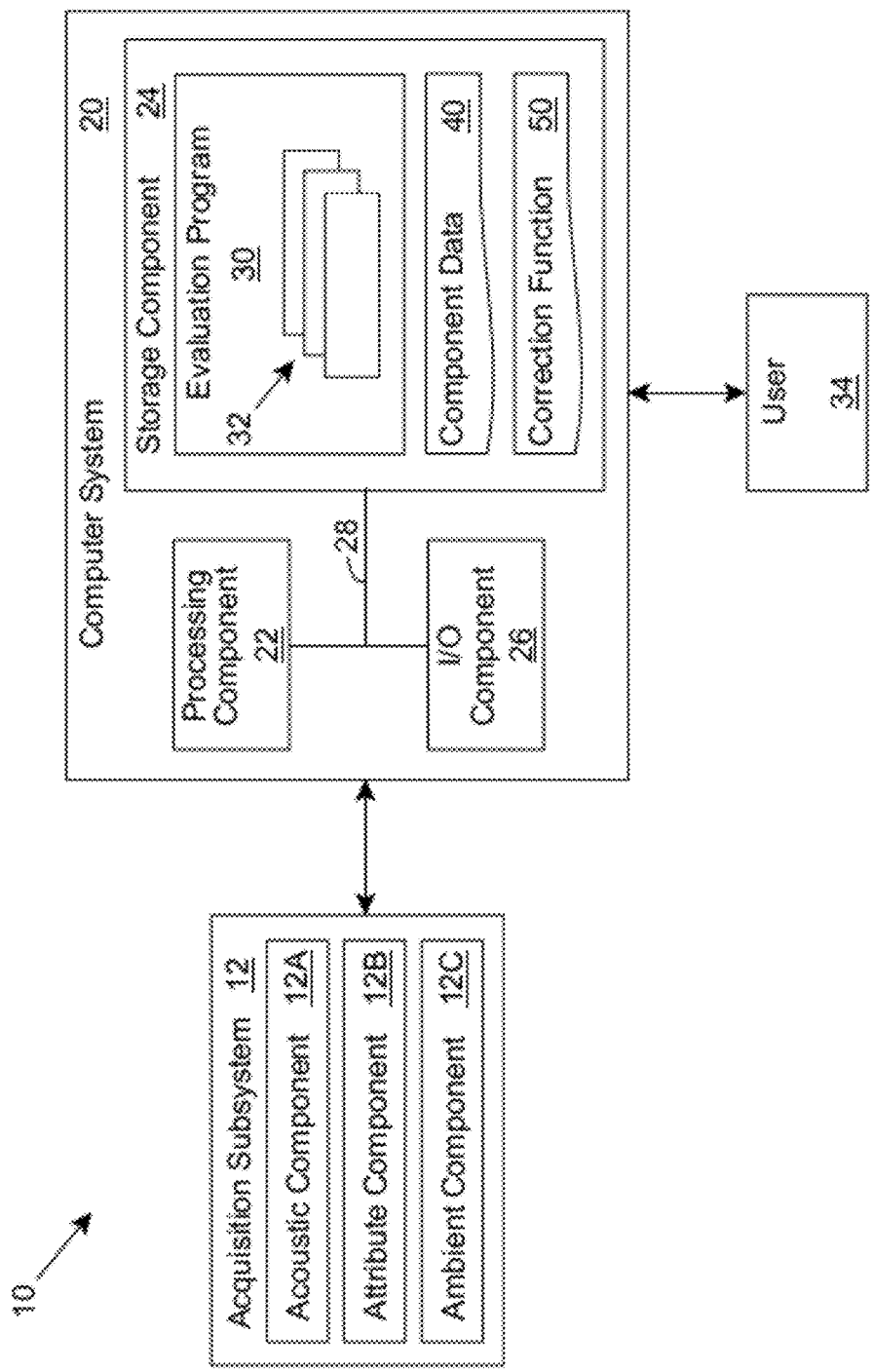
FIG. 1 shows an illustrative acoustic-based rotating component analysis system according to an embodiment.

Turning to the drawings, FIG. 1 shows an illustrative acoustic-based rotating component analysis system 10 according to an embodiment. To this extent, system 10 includes a computer system 20 that can receive data, including acoustic data corresponding to a target rotating component, from acquisition subsystem 12 and perform a process described herein in order to analyze one or more attributes of the target rotating component using the acoustic data. In particular, computer system 20 is shown including an evaluation program 30, which makes computer system 20 operable to analyze one or more attributes of the target rotating component using the acoustic data by performing a process described herein.

Computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, processing component 22 executes program code, such as evaluation program 30, which is at least partially fixed in storage component 24. While executing program code, processing component 22 can process data, which can result in reading and/or writing transformed data from/to storage component 24 and/or I/O component 26 for further processing. Pathway 28 provides a communications link between each of the components in computer system 20. I/O component 26 can comprise one or more human I/O devices, which enable a human user 34 to interact with computer system 20 and/or one or more communications devices to enable a system user 34 to communicate with computer system 20 using any type of communications link. To this extent, evaluation program 30 can manage a set of interfaces (e.g., graphical user interface(s), application program interface, and/or the like) that enable human and/or system users 34 to interact with evaluation program 30. Further, evaluation program 30 can manage (e.g., store, retrieve, create, manipulate, organize, present, etc.) the data, such as component data 40, using any solution.

In any event, computer system 20 can comprise one or more general purpose computing articles of manufacture (e.g., computing devices) capable of executing program code, such as evaluation program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, evaluation program 30 can be embodied as any combination of system software and/or application software.

Further, evaluation program 30 can be implemented using a set of modules 32. In this case, a module 32 can enable computer system 20 to perform a set of actions used by evaluation program 30, and can be separately developed and/or implemented apart from other portions of evaluation program 30. As used herein, the term "component" means any configuration of hardware, with or without software, which implements the actions described in conjunction therewith using any solution, while the term "module" means program code that enables a computer system 20 to implement the actions described in conjunction therewith using any solution. When fixed in a storage component 24 of a computer system 20 that includes a processing component 22, a module is a substantial portion of a component that implements the actions. Regardless, it is understood that two or more components, modules, and/or systems may share some/all of their respective hardware and/or software. Further, it is understood that some of the functionality discussed herein may not be implemented or additional functionality may be included as part of computer system 20.

When computer system 20 comprises multiple computing devices, each computing device can have only a portion of evaluation program 30 fixed thereon (e.g., one or more modules 32). However, it is understood that computer system 20 and evaluation program 30 are only representative of various possible equivalent computer systems that may perform a process described herein. To this extent, in other embodiments, the functionality provided by computer system 20 and evaluation program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when computer system 20 includes multiple computing devices, the computing devices can communicate over any type of communications link. Further, while performing a process described herein, computer system 20 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

As discussed herein, system 10 is configured to perform an acoustic-based analysis of a rotating component of a machine during operation of the machine. To this extent, acquisition subsystem 12 is shown including an acoustic component 12A, which can comprise a set of acoustic sensors configured to acquire the acoustic data. Computer system 20 can process the acoustic data to determine whether an evaluated condition is present. For example, when the evaluated condition is present in the rotating component, operation of the component can emit sounds having an identifiable acoustic signature. Computer system 20 can evaluate the acoustic data for the presence of the corresponding acoustic signature of the evaluated condition.

To this extent, the acoustic sensor(s) in acoustic component 12A are sensitive to acoustic signals for a range of frequencies including the frequencies within which the acoustic signature(s) will be found. In an embodiment, an acoustic sensor is configured to enhance the acoustic signals in the range of frequencies relevant to the acoustic signature(s) with respect to acoustic signals outside of the range of frequencies. For example, the acoustic sensor can magnify acoustic signals received in the relevant range of frequencies and/or suppress/reduce acoustic signals received outside of the relevant range of frequencies.

Additionally, acoustic signals generated by other components of the machine or other ambient noises (e.g., an adjacent machine) can reduce the accuracy of evaluation of the acoustic data. To this extent, an acoustic sensor can be configured to enhance acoustic signals received from a relevant area. For example, the acoustic sensor can be configured to receive acoustic signals primarily emanating from a narrowly focused directional area, accentuate acoustic signals received from a narrowly focused directional area with respect to acoustic signals received from other directions, attenuate acoustic signals received from other directions with respect to acoustic signals received from a narrowly focused directional area, and/or the like.

Figure 2:
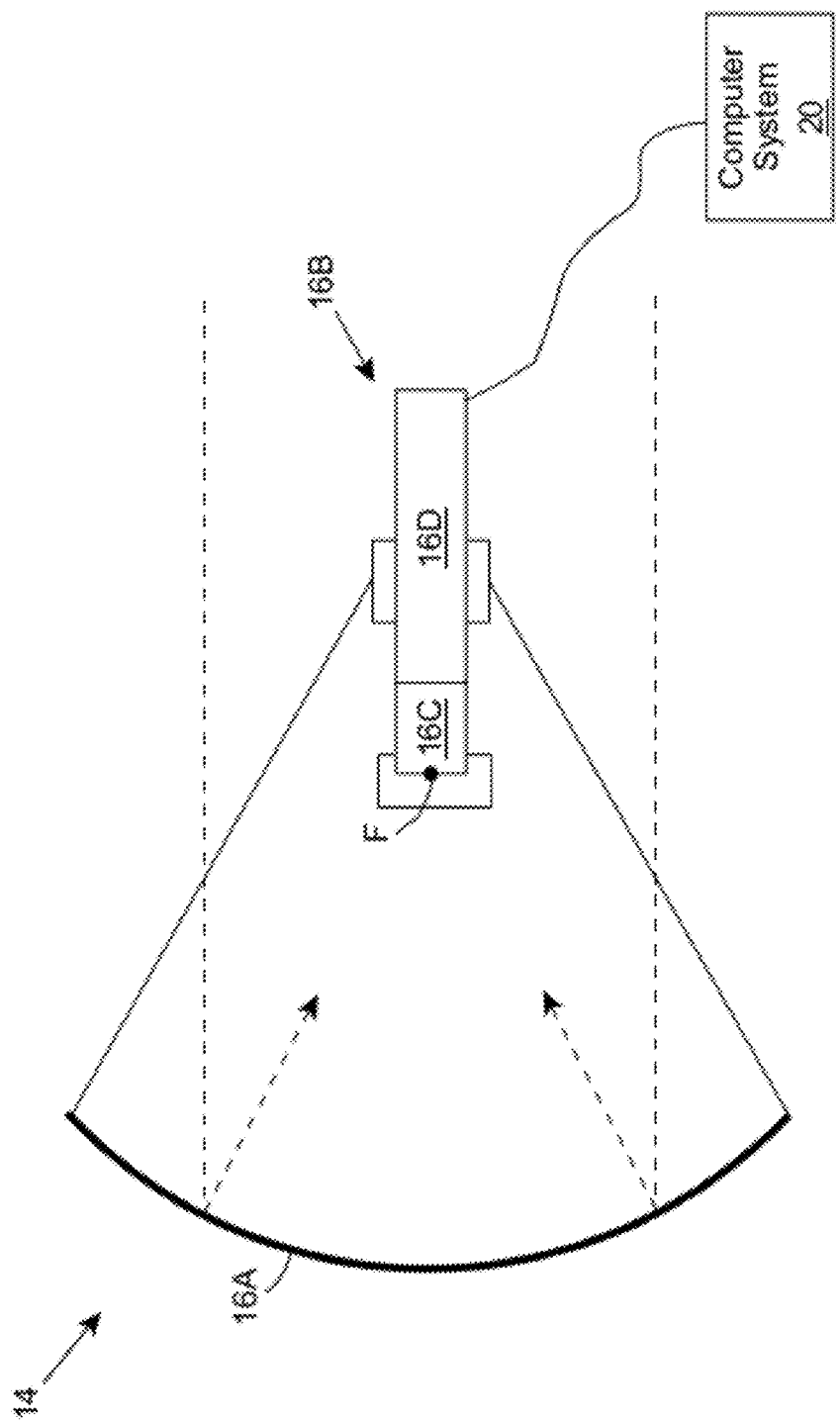
FIG. 2 shows an illustrative acoustic sensor according to an embodiment.

FIG. 2 shows an illustrative acoustic sensor 14 according to an embodiment. Acoustic sensor 14 is a parabolic microphone, which includes a reflective antenna 16A and a transducer 16B. As illustrated, reflective antenna 16A reflects acoustic signals received from a narrowly focused directional area toward a focal point, F, thereby providing mechanical amplification of any on-axis/nearly on-axis sounds arriving at acoustic sensor 14. While a parabolic reflective antenna 16A is shown and described, it is understood that a spherical or other shaped antenna 16A also can be used. Transducer 16B is configured to convert acoustic signals into electrical energy. To this extent, transducer 16B can include a microphone 16C and a preamplifier 16D. Microphone 16C can be located such that its sensing area (e.g., diaphragm) is located at focal point F. Microphone 16C can comprise any type of microphone including, but not limited to, a condenser microphone, an electret microphone, a micro-electro mechanical systems (MEMS) microphone, and/or the like. Preamplifier 16D can increase the output voltage of microphone 16C to a stronger, more usable level for further processing, e.g., by computer system 20. It is understood that preamplifier 16D also can provide an appropriate amount of analog anti-alias filtering in an embodiment.

Acoustic sensor 14 can hold transducer 16B in place using any solution. For example, acoustic sensor 14 can include a plurality of struts, each of which is attached to reflective antenna 16A and transducer 16B with a corresponding set of clamps. Acoustic sensor 14 can further include one or more protective elements. For example, microphone 16C can be covered by a protective screen. Further, transducer 16B can be enclosed within a housing configured to protect transducer 16B during outdoor operation. Transducer 16B can be operationally connected to one or more additional components, such as computer system 20, using any solution, e.g., a set of wires connected to preamplifier 16D, or the like.

As is known, a parabolic microphone, such as acoustic sensor 14, comprises a high gain directional antenna. To this extent, acoustic sensor 14 can be configured to enhance acoustic signals in a range of relevant frequencies and/or enhance acoustic signals received from a directional area corresponding to the location of the rotating component. For example, acoustic sensor 14 can be configured with a shape and focal length such that an acceptance angle of the microphone 16C is matched to the reflective antenna 16A, thereby providing much higher gain for the relevant acoustic signals for the same physical sized antenna 16A. In some applications, the acoustic signals of an evaluated condition can be much softer than ambient noises. In this case, acoustic sensor 14 can provide sufficient gain for the relevant frequencies and isolation from sounds emanating from other sources to enable accurate evaluation for the presence of the condition in the target rotating component.

In an embodiment, the directional area is narrowly focused on the rotating component. For example, acoustic sensor 14 can be configured to enhance acoustic signals emanating from a main directional area defined by azimuth and elevation beam widths of less than approximately ten degrees. Further, a cross section of the main directional area at the location of the rotating component can comprise a size that includes the rotating component, but does not include adjacently located sound sources (e.g., other rotating components). Use of an acoustic sensor, such as acoustic sensor 14, with acute beam widths and high gain enables the acoustic sensor 14 to be placed further from the location of the rotating component while still being capable of capturing acoustic data that is sufficient for effective evaluation of the rotating component.

While a parabolic microphone, such as acoustic sensor 14, is shown and described herein, it is understood that any alternative component for acquiring highly directional acoustic signals and/or providing high gain to acoustic signals can be used. For example, a laser vibrometer can be used to acquire acoustic data. In a laser vibrometer, a laser is projected onto some surface of a target object and the reflected light is analyzed for changes. In a still, non-vibrating object, no significant changes are present in the return signal. However, vibrations of the target object will deflect the laser light, causing detectable variations in the light returned to the detector. These variations can be directly translated to identical signal patterns acquired by a microphone detecting the equivalent sound. Similarly, various experiments have used polarized light reflected from a surface to show interference patterns, which also vary with vibration and distortion.

Returning to FIG. 1, acquisition subsystem 12 can include one or more additional components for acquiring data regarding the target rotating component, the machine on which the rotating component is operating, the environment of the rotating component, and/or the like. To this extent, acquisition subsystem 12 is shown including an attribute component 12B. Attribute component 12B can include one or more sensing devices configured to acquire attribute data on the rotating component and/or the machine on which the rotating component is operating. For example, attribute component 12B can include a device, such as a radio frequency identification (RFID) tag reader, which can acquire a unique identifier for the rotating component and/or machine, e.g., by reading a RFID tag associated therewith. When the machine is moving through an inspection area (e.g., when the machine is a vehicle), attribute component 12B can further acquire data detecting the presence of the machine, data on the speed and/or direction that the machine is moving, data on the distance to the machine, and/or the like. Additionally, attribute component 12B can include one or more devices configured to capture other types of data, such as an imaging device (e.g., infrared or visible) configured to capture image data on the machine and/or rotating component, a vibrometer and/or accelerometer for capturing vibration data, and/or the like. Regardless, the attribute data acquired by attribute component 12B can be provided to computer system 20 for further processing.

Acquisition subsystem 12 can further include an ambient component 12C, which can acquire ambient data regarding the environment in which system 10 and/or the target rotating component is operating. For example, ambient component 12C can include a thermometer for acquiring temperature data, a hygrometer for acquiring humidity data, a barometer for measuring atmospheric pressure, an anemometer for measuring wind direction/speed, a light sensor for measuring the lighting conditions, a visibility sensor for measuring visibility, and/or the like. Regardless, the ambient data acquired by ambient component 12C can be provided to computer system 20 for further processing.

Figure 3:
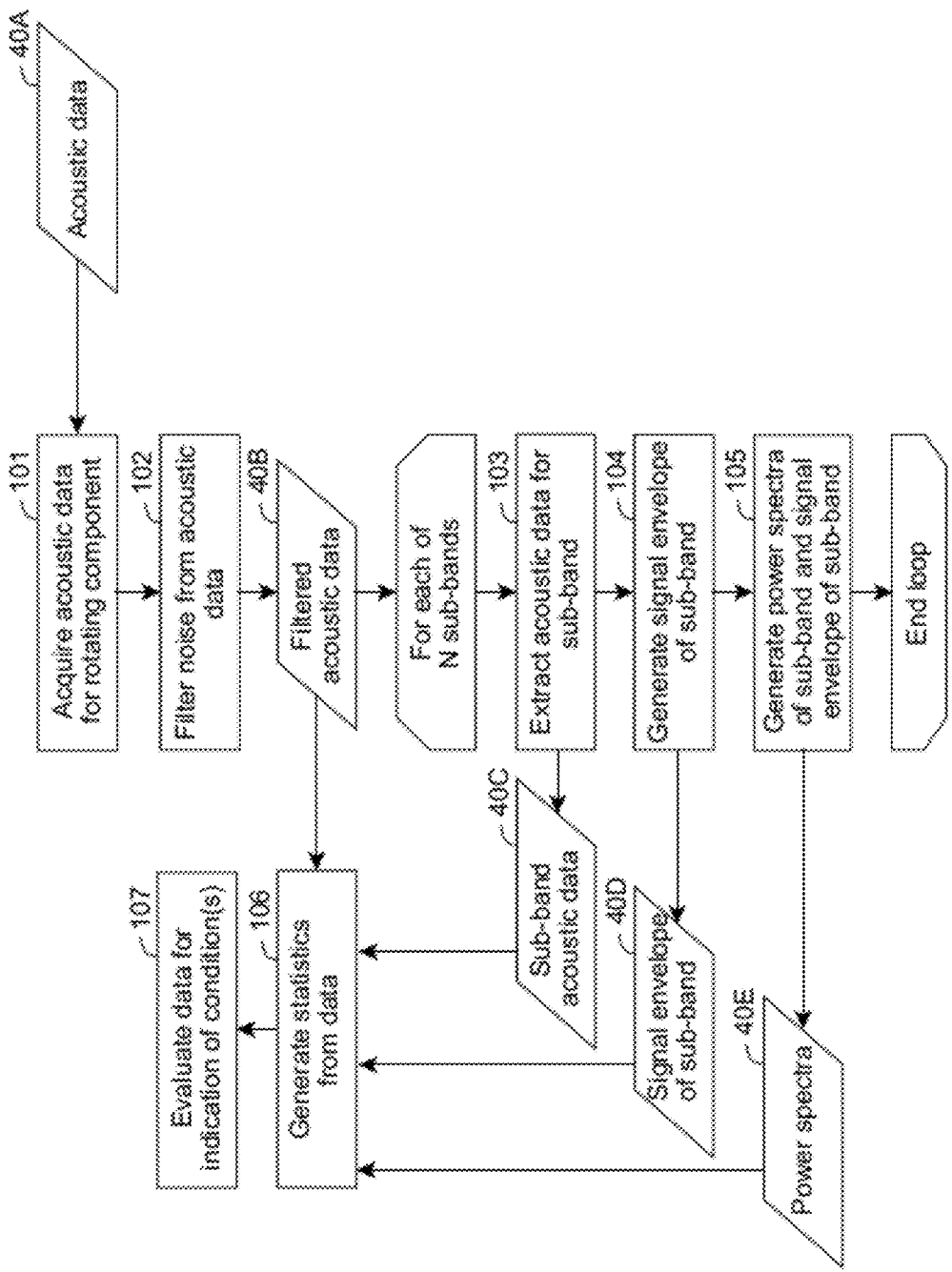
FIG. 3 shows an illustrative process for evaluating a rotating component using acoustic data according to an embodiment.

Computer system 20 can extract a wide variety of different signal features from acoustic data acquired for a rotating component. The particular signal features that are relevant can vary based on the application and the rotating component being evaluated. FIG. 3 shows an illustrative process for evaluating a rotating component using acoustic data according to an embodiment, which can be implemented by computer system 20 (FIG. 1). Referring to FIGS. 1 and 3, in action 101, computer system 20 acquires acoustic data 40A corresponding to a rotating component of a machine, e.g., from acoustic component 12A of acquisition subsystem 12. Computer system 20 can acquire the acoustic data 40A in real time, e.g., as it is acquired by acoustic component 12A or after an acoustic sample is acquired by acoustic component 12A. The acoustic data 40A can embody the acoustic signal captured during operation of the rotating component using any solution. For example, the acoustic data 40A can comprise a data file that encodes the audio using a pulse-code modulation (PCM) format, or the like.

Regardless, in action 102, computer system 20 filters unwanted noise from the acoustic data to generate filtered acoustic data 40B. For example, computer system 20 can implement a noise filter to remove background noise from the acoustic data 40A. In an embodiment, computer system 20 generates a noise model for a particular deployment location. In this case, computer system 20 can implement an adaptive algorithm that continually computes and updates the long term statistics and spectral characteristics of the background noise of the deployment location. Computer system 20 can use the noise model to generate a set of adaptive thresholds and matched digital filters and utilize these thresholds and filters to detect, enhance, and extract signals of interest that are embedded in the noise. For example, computer system 20 can perform statistical averaging on the background noise detected over an extended period of time, and use an acceptance range, e.g., of +/− two standard deviations from a computed mean for the background noise to establish a range of acceptance values. Subsequently, any values outside of the range of acceptance values can identified as a signal of interest. Additionally, computer system 20 can implement a band-pass filter, which removes the acoustic data corresponding to frequencies outside of a spectral area of interest, e.g., 10 Hz to 50 kHz. In action 106, computer system 20 can generate a set of statistics based on the filtered acoustic data 40B as discussed further herein.

In addition to evaluating the entire filtered acoustic data 40B, computer system 20 can separately process and evaluate the acoustic data for a set of N sub-bands. To this extent, in action 103, computer system 20 extracts sub-band acoustic data 40C for a sub-band in the set of N sub-bands from the filtered acoustic data 40B. Each sub-band can correspond to a unique region of the spectral area of interest. In action 106, computer system 20 can generate a set of statistics based on the sub-band acoustic data 40C as discussed further herein.

Additionally, in action 104, computer system 20 can generate a signal envelope of the sub-band 40D from the sub-band acoustic data 40C for the sub-band. For example, computer system 20 can divide the sub-band acoustic data 40C into a top portion and a bottom portion with respect to a central level. Computer system 20 can invert and mathematically superimpose the bottom portion on the top portion to generate a signal which is the sum of the absolute values of the top and bottom portions. Computer system 20 can trace the maximum levels along the summed signal to obtain the signal envelope of the sub-band 40D. In action 105, computer system 20 can generate a power spectrum of the sub-band of the sub-band acoustic data 40C and generate a power spectrum of the signal envelope of the sub-band 40D. The power spectrum graphs the relative power in a given signal at specific frequencies. In action 106, computer system 20 can generate a set of statistics based on each of the signal envelope of the sub-band 40D and the power spectra 40E of the sub-band and the corresponding signal envelope, respectively.

As discussed herein, in action 106, computer system 20 can generate a unique set of statistics for various component data 40A-40E generated from the acoustic data acquired during operation of a rotating component. The set of statistics can include various statistics, such as a minimum/maximum signal, an average signal, root mean square (RMS), kurtosis, sum of points, variance, and/or the like. The particular set of statistics generated for each type of component data 40A-40E generated from the acoustic data can be selected based on a theoretical and/or practical determination of the relevant statistical values for identifying a condition of the rotating component using the particular type of component data 40A-40E. The resulting sets of statistics can include the same and/or different group of statistics for one or more types of component data 40A-40E.

In action 107, computer system 20 evaluates the statistical data generated in action 106 for an indication of the presence of one or more conditions being evaluated for the rotating component. In order to reliably determine the presence of a condition (e.g., fault), computer system 20 can use a set of condition criteria, e.g., characteristics, circumstances, thresholds, and/or the like, which together indicate the presence of the condition. Additionally, computer system 20 can use a similar set of confounding criteria, which are associated with confounding variables and signals to eliminate such irrelevant portions of the signal. Illustrative evaluated conditions for the rotating component include faulty operating performance, proper performance, over speed, under speed, slipping, and/or the like. In a rail implementation described further herein, the evaluated conditions can include a spalled bearing and a wheel flat, while a confounding condition can comprise a rail/vehicle generated acoustic creak. Computer system 20 can store a result of the evaluation for later use and/or generate a signal to initiate one or more responses in response to determining that the evaluated condition is present.

The set of condition criteria and/or confounding criteria used to evaluate the acoustic data for a particular condition can be determined using any solution. For example, a user 34 can theoretically model the acoustic signatures for one or more evaluated and/or confounding conditions. The theoretical model can be used to generate a corresponding acoustic signature of the condition, which can be used to derive the corresponding set of criteria.

In an embodiment, practical experience of a user 34 and/or "known" components are utilized to generate the set of criteria for a corresponding condition (evaluated or confounding). For example, a user 34 sufficiently experienced to identify the sounds corresponding to a particular condition and a sound sample of a component known to have the condition can be used by a designer to generate the set of criteria. The user 34 can assist in identifying a relevant sub-band of the acoustic data, determining the particular sound/series of sounds that provide the indication, and/or the like. A designer can use this information to explore the use of various tools which are likely to enhance the correct portions of the signal and make it easily distinguishable from background sounds.

Figure 4:
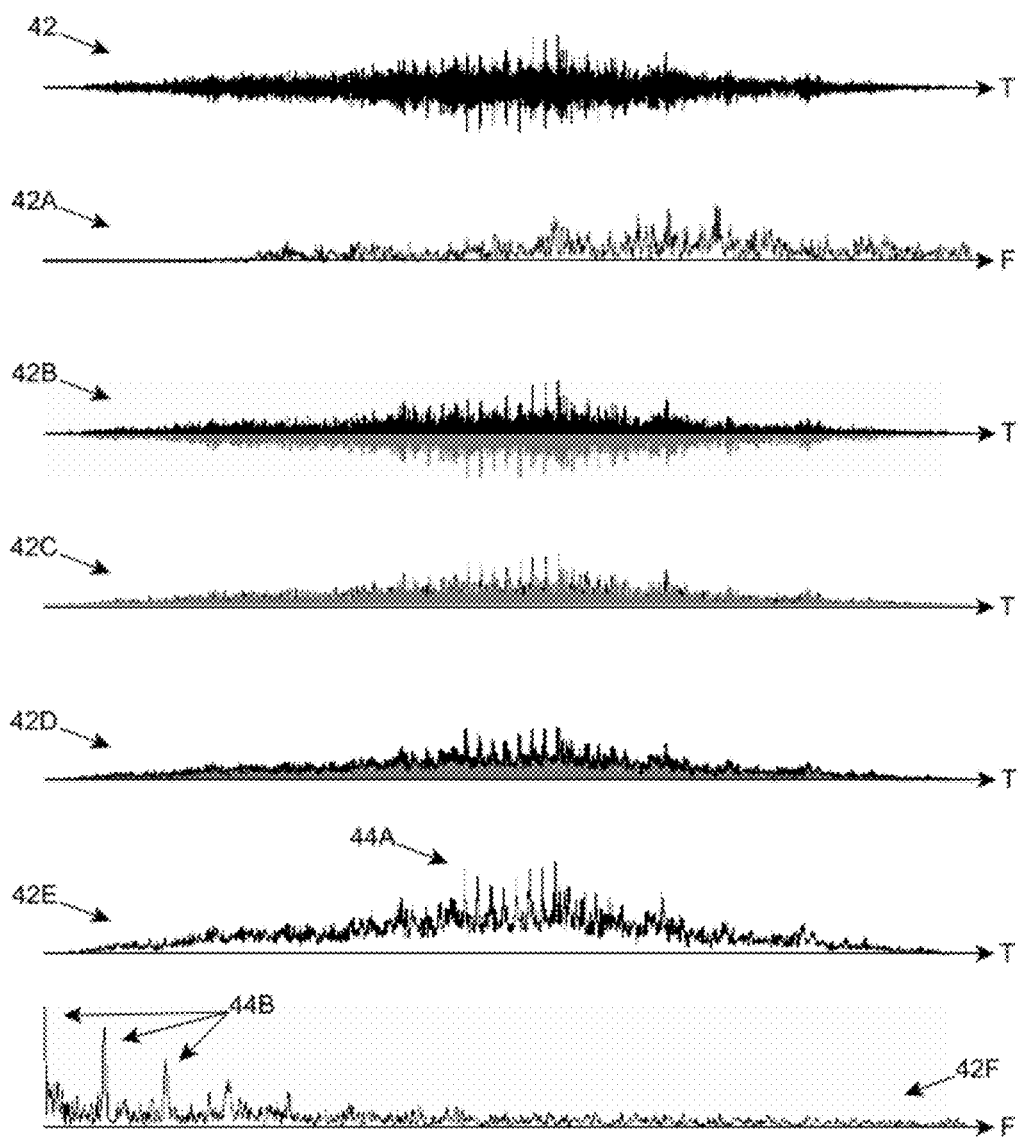
FIG. 4 shows an illustrative series of acoustic signal processing to derive a set of criteria for a condition according to an embodiment.

FIG. 4 shows an illustrative series of acoustic signal processing to derive a set of criteria for a condition according to an embodiment. Initially, an acoustic sample 42 known to include sounds corresponding to the condition (e.g., a spalled bearing of a rail wheel in this example) is obtained over a time period. Acoustic sample 42 does not include a clear indication of any unique signature corresponding to the condition. As a result, a power spectrum 42A of the frequencies within acoustic sample 42 is generated.

However, the power spectrum 42A also does not include a clear signature corresponding to the condition. As a result, an envelope of the signal 42E over the time period is generated. Generation of the envelope of the signal 42E can be implemented by selecting a central level of the signal and dividing the signal over the time period into a top portion and a bottom portion as shown in 42B. Subsequently, as illustrated in 42C, the bottom portion of the signal over the time period is inverted so that what amounted to negatives with respect to the top portion's orientation become positives. As illustrated in 42D, a signal that is the sum of the absolute values of the two halves is generated over the time period. The signal envelope 42E over the time period is then generated by tracing the maximum levels along the summed signal 42D. The net effect of generating the signal envelope 42E is to enhance or exaggerate trends over the time period that may be difficult (or impossible) to effectively identify in the original signal 42 and/or its power spectrum 42A.

While clearly derived from acoustic sample 42, signal envelope 42E includes a portion 44A of the time period that appears noticeably different from the signal envelope 42E over the remainder of the time period. Additionally, by generating a power spectrum 42F of the frequencies within the signal envelope 42E, a strongly enhanced set of signals 44B (e.g., sharp spiked peak amplitudes) is present. As a result, the power spectrum 42F can be generated and evaluated to determine whether the condition is present in the rotating component. To this extent, in order to evaluate a rotating component for this particular condition, a spalled bearing of a rail wheel in this example, computer system 20 (FIG. 1) can obtain data representing an acoustic signal in an appropriate signal band that was acquired during operation of the rotating component, generate the signal envelope of the acoustic signal, generate a power spectrum of the signal envelope, and evaluate the power spectrum to determine if there are peaks in the power spectrum over a determined level and/or at certain frequencies. It is understood that this process is only illustrative of many possible processes. For example, some conditions can be indicated by changes in the overall frequency patterns (e.g., skewing or kurtosis), by extremity of levels (e.g., range of variance), and/or the like. Additionally, while only a single acoustic sample 42 is shown and discussed, it is understood that multiple acoustic samples 42 including acoustic data indicating the same condition can be evaluated to determine the parameters indicating that the condition is present in the rotating component.

In order to accurately analyze and compare acoustic signals, the response parameters (e.g., sensitivity, frequency response, and/or the like) of acoustic sensors (e.g., microphones) used to acquire the acoustic data should be sufficiently similar. For example, a sufficient difference between the response parameters of an acoustic sensor that acquired the acoustic sample 42 and an acoustic sensor 14 (FIG. 2) that is deployed in the field can result in sufficiently different acoustic data to cause computer system 20 to make an inaccurate determination regarding the presence or absence of a condition. Obtaining acoustic sensors that are physically sufficiently close in their respective response parameters can be very expensive and time consuming depending on the type of acoustic sensor and the level of similarity required to achieve a sufficient match.

In an embodiment, computer system 20 (FIG. 1) manipulates the acoustic data acquired by an acoustic sensor, such as acoustic sensor 14 (FIG. 2), to adjust for differences in the acoustic data from the acoustic data that would have been acquired by an exemplar acoustic sensor. For example, an exemplar acoustic sensor can be selected from multiple acoustic sensors. In a controlled test and matching environment, a series of sounds can be generated and recorded using the exemplar acoustic sensor. Subsequently, an acoustic sensor to be deployed as part of a system 10 (FIG. 1) can record the same series of sounds in the controlled test and matching environment.

Figure 5:
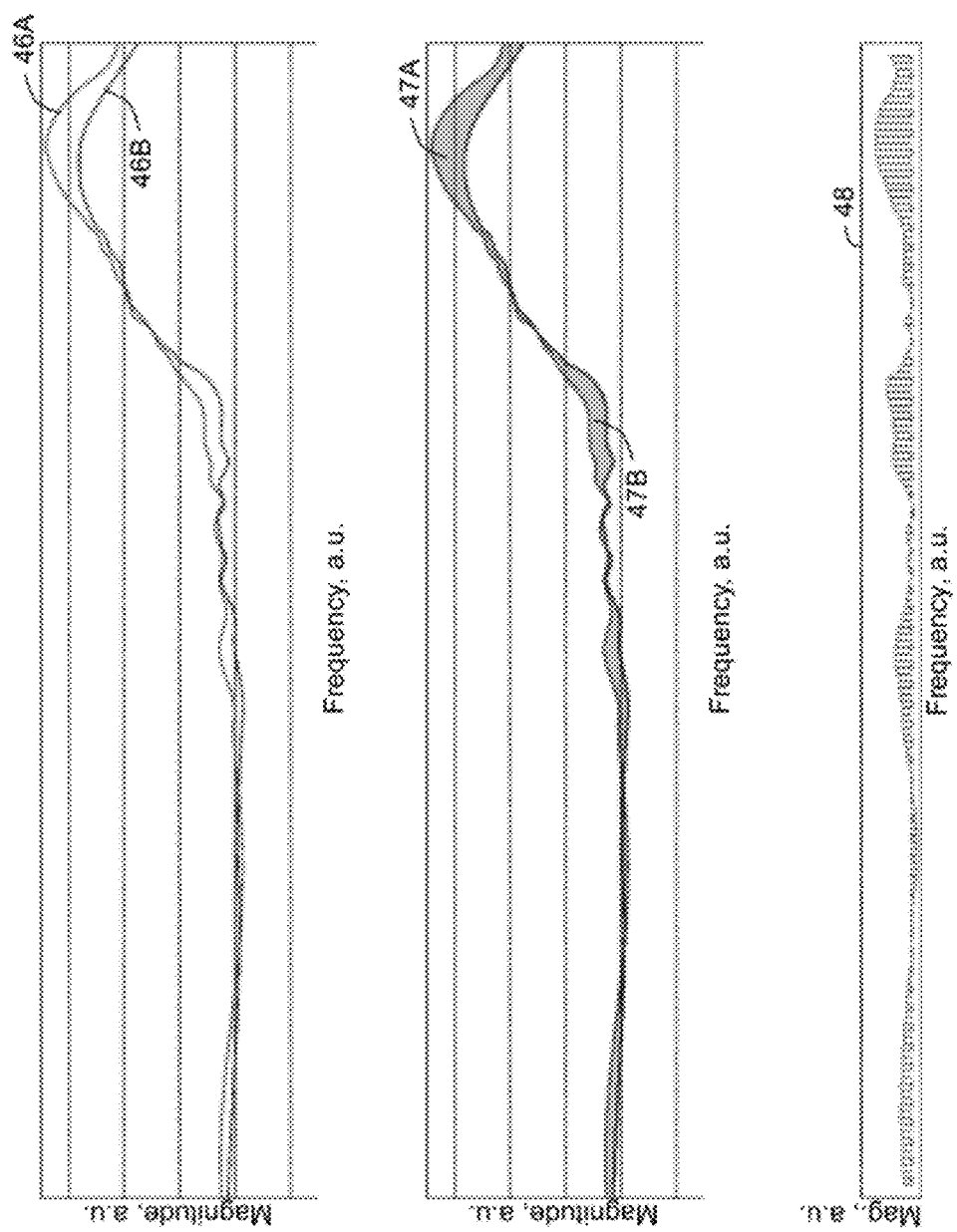
FIG. 5 shows a series of graphs that can be used to adjust for differences in acquired acoustic data for a pair of acoustic sensors according to an embodiment.

FIG. 5 shows a series of graphs that can be used to adjust for differences in acquired acoustic data for a pair of acoustic sensors according to an embodiment. In particular, the frequency response 46A of an exemplar acoustic sensor and the frequency response 46B of the acoustic sensor to be deployed in system 10 can be graphed. The differential areas, such as areas 47A, 47B, between the two frequency responses 46A, 46B can be identified, and a graph 48 of the differential areas 47A, 47B can be generated. As illustrated, graph 48 may include areas in which the exemplar acoustic sensor had a higher frequency response and areas in which the acoustic sensor to be deployed had a higher frequency response.

Using graph 48, a correction function 50 (FIG. 1) for the acoustic sensor to be deployed can be generated, e.g., by measuring the differential at regular, closely spaced intervals and normalizing to a zero level. The correction function 50 can be deployed together with the acoustic sensor to a system 10 and applied to the acoustic data acquired by the acoustic sensor during operation of system 10. For example, computer system 20 can store and apply the correction function 50 prior to performing additional processing on data corresponding to an acoustic signal acquired by the acoustic sensor. It is understood that this process is only illustrative, and computer system 20 can implement any solution to ensure that the acoustic data is sufficiently close to acoustic data used to determine the evaluation parameters for the various conditions.

After deployment, the acoustic sensor can be periodically verified and re-calibrated using any solution. For example, a signal generation device (e.g., one or more loudspeakers coupled to an electronic signal generator or to a high-quality recording of a test signal pattern) can be placed opposite the acoustic sensor, within the directional area of the acoustic sensor. The system 10 can be placed in a test/calibration mode, in which the signal generation device is activated and generates a test signal pattern, which is acquired by the acoustic sensor(s). Computer system 20 can compare the acquired acoustic data to baseline acoustic data previously acquired by the acoustic sensor (e.g., when first deployed) for the same test pattern. If computer system 20 finds a significant deviation between the acoustic data, computer system 20 can indicate that a potential problem exists in one or more components of the acoustic sensor. In an embodiment, the signal generation device is deployed as part of system 10, and computer system 20 periodically performs the test/calibration in an automated manner. Alternatively, the process can be performed manually, e.g., after a predetermined period, in response to a change in accuracy of the evaluation, and/or the like.

Figure 6:
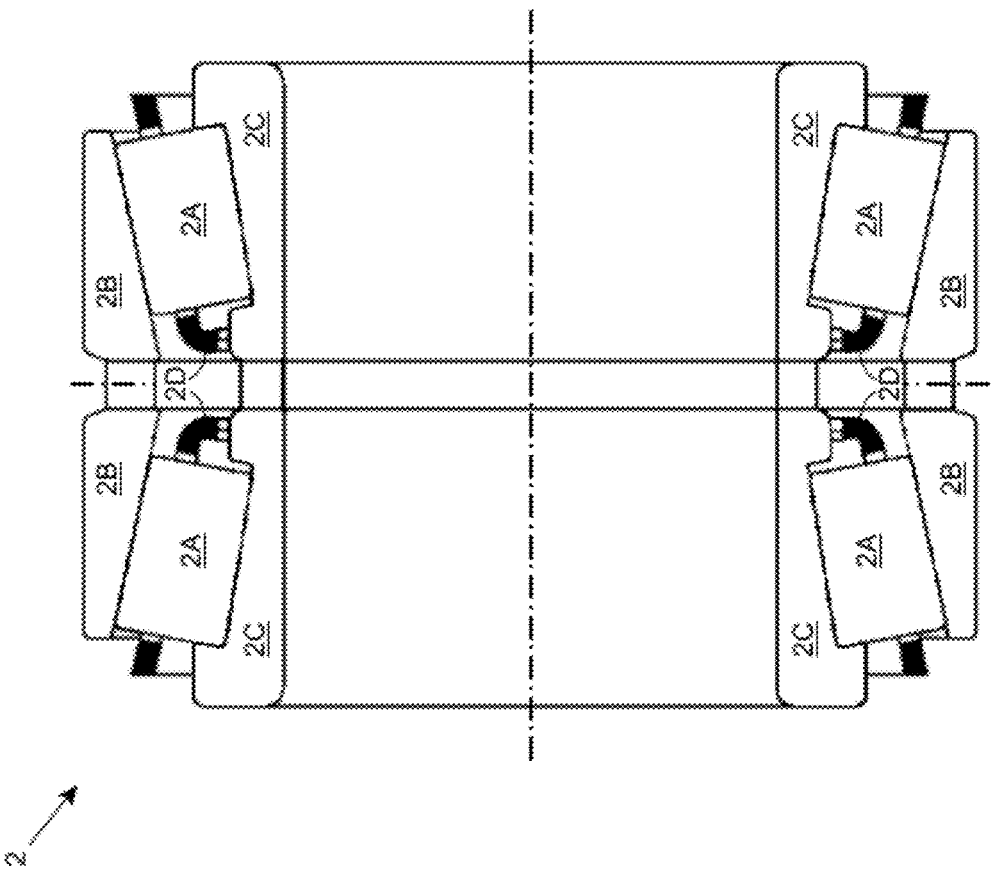
FIG. 6 shows a cross-section of an illustrative railroad wheel bearing.

In an illustrative application, system 10 can be configured and deployed to evaluate a set of conditions of one or more rotating components of a rail vehicle during operation of the rail vehicle. For example, system 10 can evaluate a railroad wheel bearing for the presence of a condition, such as spalling, which can lead to failure of the bearing. To this extent, FIG. 6 shows a cross-section of an illustrative railroad wheel bearing 2, which can be evaluated for the presence of a set of conditions using system 10 according to an embodiment. Bearing 2 is a roller bearing, and includes a set of rollers 2A, each of which is held in place by a cup (sleeve) 2B and rides on a cone (seat) 2C. A bearing cage 2D is included to minimize side-to-side movement and center the bearing 2. Collectively, the internal areas of the cup 2B and cone 2C are referred to as the bearing races (raceways).

When roller bearings, such as bearing 2 are implemented on a rail wheel, acoustic data for a full rotation of the rail wheel is generally not required to detect a fault in the bearing 2. In particular, as the rail wheel rotates, various portions of the cup 2B and cone 2C pass over, or are passed over by, the rollers 2A. To this extent, all rollers 2A perform several full rotations during a single full rotation of the rail wheel. Additionally, all portions of the cup 2B and cone 2C have passed over, or been passed over by, one or more of the rollers 2A after the wheel moves a distance equivalent to the intra-roller spacing. A defect in any one of the components of bearing 2 will cause the structure to vibrate in a characteristic manner, with the vibrations cycling at frequencies proportional to the overall speed of the rail wheel. Depending on the design of the bearings 2 and their sizes, the precise frequencies of repetition for a defect on a roller 2A, cup 2B, cone 2C, or the like, can vary to some extent. Regardless, sufficient characteristic acoustic signals for detecting and diagnosing a condition (e.g., defect) of a rail bearing 2 can be obtained in considerably less than a single revolution of a rail wheel.

Figure 7:
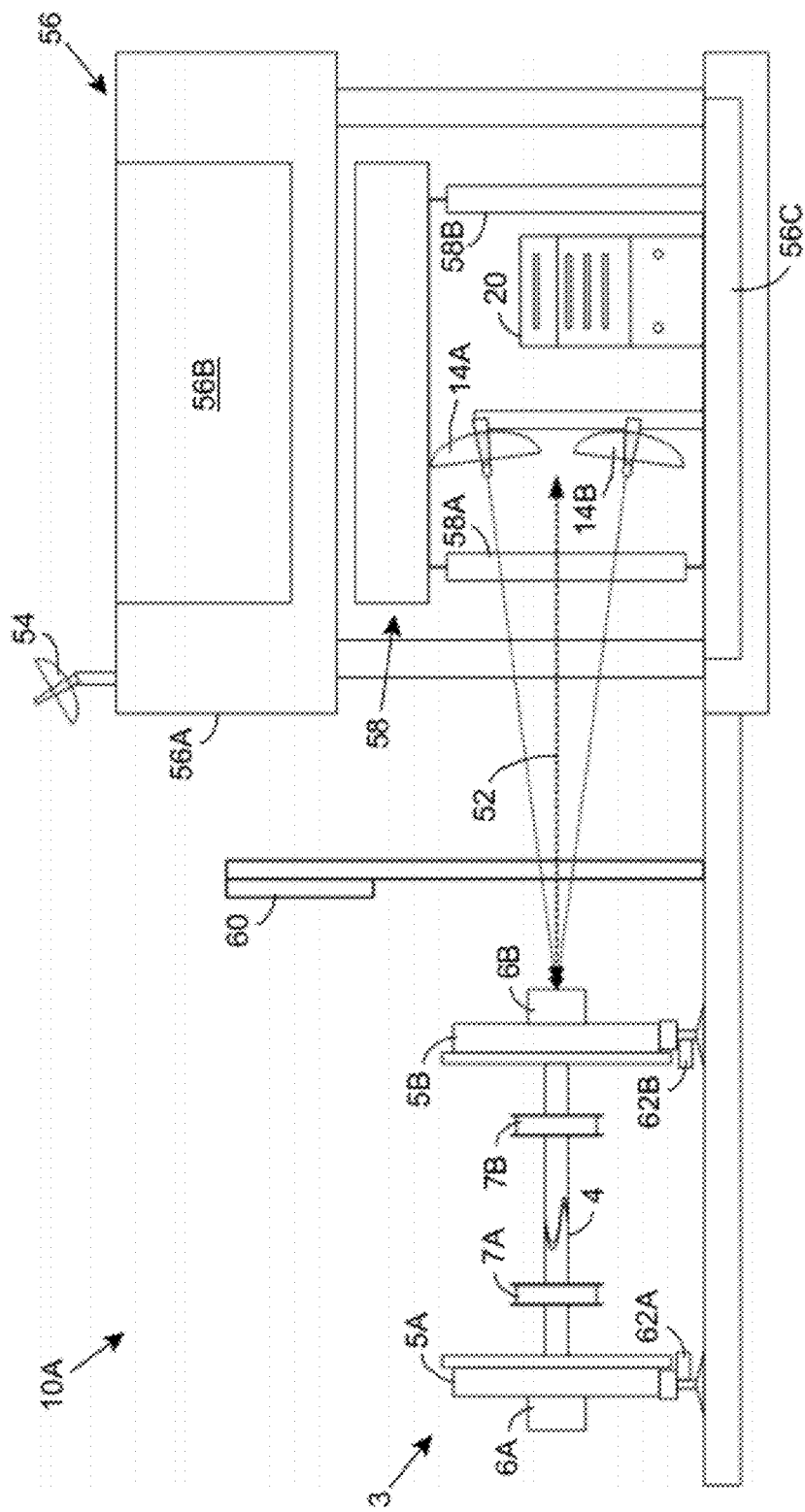
FIG. 7 shows an illustrative implementation of the system of FIG. 1 for evaluating a set of rotating components of a rail vehicle according to an embodiment.

FIG. 7 shows an illustrative implementation 10A of system 10 (FIG. 1) for evaluating a set of rotating components of a rail vehicle (e.g., locomotive, rail car, or any other type of rolling stock) according to an embodiment. The set of rotating components can include any number of rotating components of the rail vehicle, including but not limited to, rail bearings, rail wheels (e.g., wheel flats or out of round), engine bearings, turbo charger bearings, brake assemblies, and/or the like. System 10 can be deployed adjacent to a portion of a mainline track or a slower speed track, and can be configured to identify a rotating component of a rail vehicle exhibiting one or more conditions known to be precursors for failure. System 10 can identify the condition(s) when the rotating component continues to have sufficient operating time to enable non-disruptive actions to be scheduled and performed (e.g., removal of rotating component from service) prior to failure of the rotating component.

Acoustic component 12A (FIG. 1) is shown including a pair of acoustic sensors 14A, 14B. In this case, the acoustic signals acquired by each acoustic sensor 14A, 14B can be cross-correlated to enhance the target acoustic signals being emanated from the rotating component. While two acoustic sensors 14A, 14B are shown, it is understood any number of one or more acoustic sensors can be implemented in various embodiments of the invention.

Each acoustic sensor 14A, 14B is configured to acquire acoustic data corresponding to a rotating component of the rail vehicle as it moves along the rails. In an embodiment, each acoustic sensor 14A, 14B is configured to enhance acoustic signals in a range of frequencies corresponding to the condition(s) of the rotating component being evaluated and/or enhances the acoustic signals received from a directional area narrowly focused on the rotating component. To this extent, an acoustic sensor 14A, 14B can comprise a parabolic acoustic sensor, such as the acoustic sensor 14 shown and described in FIG. 2. However, it is understood that acoustic sensors 14A, 14B can comprise any type of directional and/or enhancing acoustic sensor including, for example, shotgun microphones, laser vibrometers, and/or the like. Use of directional and enhancing acoustic sensor(s) enables implementations of system 10 to comprise a small physical array size compared to previous approaches, a larger standoff distance compared to previous approaches, and an ability to monitor multiple tracks with a single set of acoustic sensors 14A, 14B.

In an illustrative embodiment, acoustic sensors 14A, 14B are configured to acquire acoustic data corresponding to the wheel assembly 3 of the rail vehicle. Wheel assembly 3 includes an axle 4, on which a plurality of wheels 5A, 5B are installed. Additionally, wheel assembly 3 includes a pair of bearing assemblies 6A, 6B and a component 7A, 7B of a brake assembly for each wheel 5A, 5B. In a more specific embodiment, acoustic sensors 14A, 14B are configured such that their respective focal points are aligned to converge at a location of wheel assembly 3 corresponding to the wheel bearing assembly 6B. In this case, acoustic sensors 14A, 14B can acquire acoustic data that enables the evaluation of components of bearing assembly 6B. However, it is understood that acoustic sensors 14A, 14B can be configured to detect acoustic signals from any combination of one or more rotating components of the wheel assembly 3. To this extent, each acoustic sensor 14A, 14B can be configured to acquire acoustic data from a distinct portion of the wheel assembly 3, e.g., bearing assembly 6B and the location at which wheel 5B contacts the rail.

In an embodiment, the direction and location of each acoustic sensor 14A, 14B is fixed. As a rail vehicle and the corresponding wheel assemblies 3 move along the rails, the location of interest, such as the wheel bearing assembly 6A, 6B moves through a target area substantially centered on the fixed direction of each acoustic sensor 14A, 14B. An acoustic sensor 14A, 14B can be selected with a corresponding size and efficiency sufficient to enable identification of the acoustic signals indicating an evaluated condition at a desired operating distance. In some applications, such as the analysis of rail wheel bearings, the acoustic signals have a relatively low power compared to other noise as the rail vehicle moves. To this extent, the acoustic sensor 14A, 14B also can be selected and/or configured to reduce an amount of extraneous noise that is detected and/or accentuate the acoustic signals within a target range of frequencies emanating from the target area.

In a more specific embodiment, each acoustic sensor 14A, 14B comprises a parabolic microphone with a spherical section of approximately twelve inches in diameter. Acoustic sensors 14A, 14B can be located at a distance 52 that provides a target area on wheel 5B that does not include components from more than one wheel assembly 3. In an embodiment, distance 52 is approximately twelve feet from the rails. Further, acoustic sensors 14A, 14B can be configured to enhance acoustic signals within a target frequency range of 10 Hz to 50 kHz, within which acoustic signals indicating the presence of a flawed bearing may be identified. In this case, each acoustic sensor 14A, 14B will have a beam width of approximately eight degrees, resulting in a primary target area on the passing rail vehicle of approximately 4.3 feet in diameter. However, it is understood that a reflective surface of another shape can be utilized, e.g., an oblong or rectangular shape, to provide a different shaped target area, depending on the application. For example, when evaluating a rail wheel 5B, the reflective surface can have an elongated horizontal area so that a full rotation of a wheel is within the target area, while the bearing assembly 6B remains outside of the target area.

In addition to acoustic sensors 14A, 14B, acquisition subsystem 12 (FIG. 1) of implementation 10A includes an attribute component 12B (FIG. 1) for acquiring additional data regarding the rail vehicles and/or wheel assemblies 3. To this extent, implementation 10A is shown including a RFID tag reader 60, which can acquire electronic identification data corresponding to a passing rail vehicle. With a unique identifier for a rail vehicle, computer system 20 can associate the evaluation of the corresponding wheel assemblies 3 with the identifier, thereby enabling tracking of the rail vehicle and wheel assemblies 3 over time. To this extent, computer system 20 can implement a process shown and described in co-pending U.S. patent application Nos. 12/043,357 and 12/171,438, both of which are incorporated by reference, to identify individual rail vehicles in a series of rail vehicles and/or forecast maintenance requirements of rail vehicles.

Additionally, implementation 10A includes a set of wheel sensors 62A, 62B, each of which is attached to a rail, and generates a signal when a rail wheel 5A, 5B is above the sensor 62A, 62B on the corresponding rail. Computer system 20 can process the signal from wheel sensors 62A, 62B to trigger activation or deactivation of one or more components of acquisition subsystem 12, synchronize the acoustic data with the passage of a specific rail wheel 5A, 5B, and/or the like.

The various components of acquisition subsystem 12 can be installed on one or both sides of the track. For example, when evaluating rail bearings and other similar components, any flaw detected on one side often is present on the other side since the bearings are virtually always installed in pairs and remain with the wheel set throughout their operation, thus being as nearly identical in manufacture, placement, and career conditions as reasonably possible. To this extent, for a given track/line, multiple acquisition subsystems 12 can be installed on alternating sides of the track/line, to periodically capture asymmetrical evaluation data of opposite sides of the rail vehicles traveling thereon.

Regardless, data acquired by acquisition subsystem 12, including acoustic sensors 14A, 14B, is provided for processing by computer system 20 as described herein. While computer system 20 is shown in physical proximity to the components of acquisition subsystem 12, it is understood that this is not necessary. For example, computer system 20 can be partially or wholly remote from acquisition subsystem 12, with the data being transmitted using a wired or wireless communications solution as it is acquired by acquisition subsystem 12. Computer system 20 performs various operations on the data to evaluate a set of conditions of the passing rotating component(s). Computer system 20 can transmit the results (and other data, such as raw data, identifying data, and/or the like) to a user 34 (FIG. 1), e.g., a remotely located storage or monitoring facility, via any communications solution, such as a satellite/wireless link 54 (e.g., for a remote installation 10A of system 10).

As illustrated, implementation 10A includes a protective enclosure 56 housing acoustic sensors 14A, 14B and computer system 20. Enclosure 56 comprises a roof 56A, which can protect a smaller equipment enclosure (e.g., shed) 58 and provide shelter to maintenance individuals. Additionally, enclosure 56 can comprise a solar cell array 56B installed on roof 56A and used in conjunction with an energy storage component to provide and/or supplement (e.g., along with an electric line or generator) power for the various components of system 10. Enclosure 56 also can comprise a drainage floor 56C, e.g., loose-rock drainage, empty space covered with gratings, and/or the like, to prevent damage to the various components due to temporary flooding. Equipment enclosure 58 can comprise a door 58A that is highly porous to sound, which permits sounds of interest to pass there through while physically screening acoustic sensors 14A, 14B from intrusion, debris, etc. Equipment enclosure 58 can further comprise a service door 58B for easy access by maintenance personnel servicing the component located within equipment enclosure 58. Additionally, equipment enclosure 58 can include heating and/or cooling equipment, if necessary.

Figure 8:
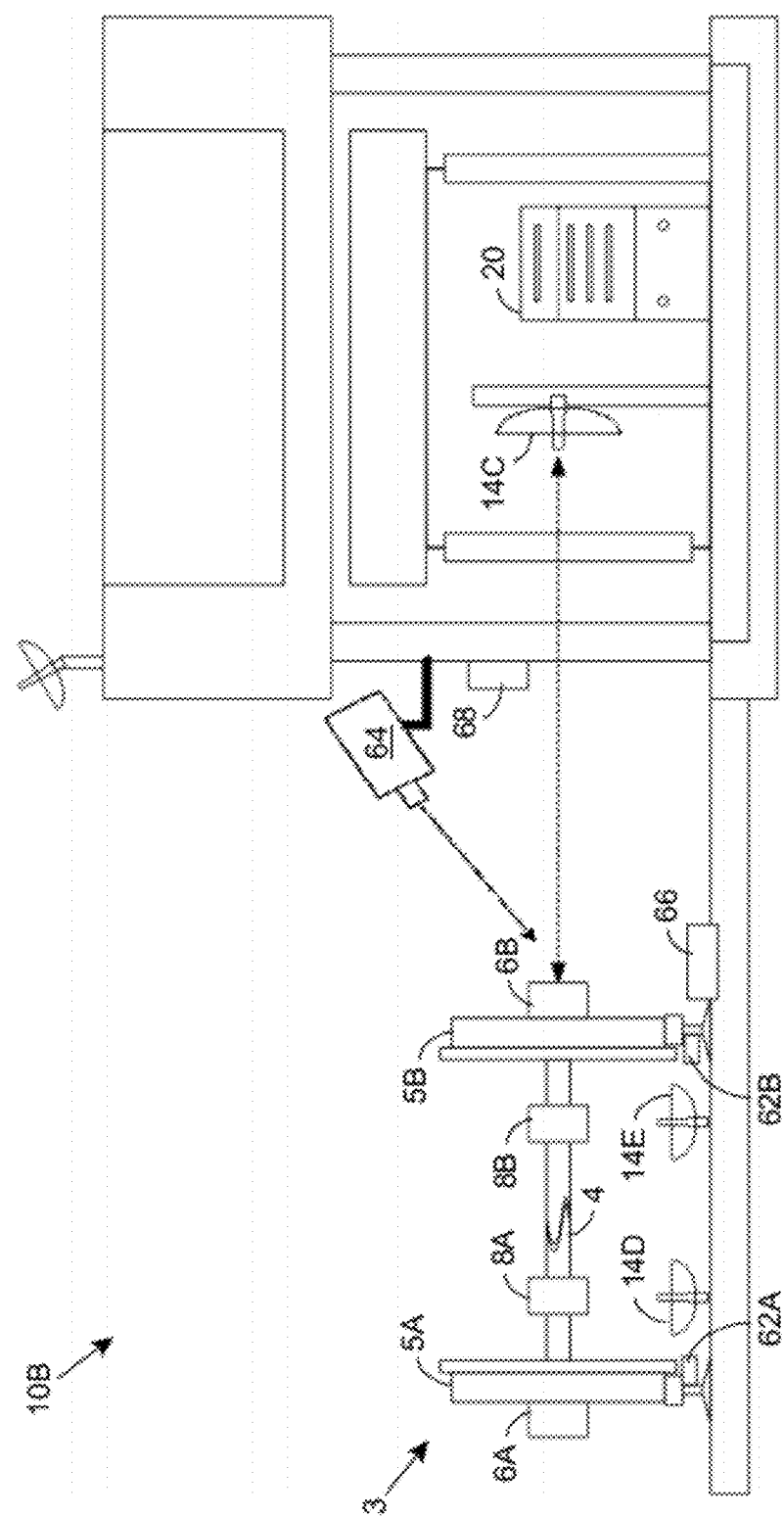
FIG. 8 shows another illustrative implementation of the system of FIG. 1 for evaluating a set of rotating components of a rail vehicle according to an embodiment.

FIG. 8 shows another illustrative implementation 10B of system 10 (FIG. 1) for evaluating a set of rotating components of a rail vehicle according to an embodiment. In implementation 10B, a single acoustic sensor 14C is used to acquire acoustic data for a corresponding bearing assembly 6B of a wheel assembly 3. Additionally, a pair of acoustic sensors 14D, 14E are configured to acquire acoustic data for in-board bearings 8A, 8B, respectively, of the wheel assembly 3.

Additionally, the attribute component 12B (FIG. 1) of implementation 10B includes an imaging device 64 configured to acquire image data corresponding to the rail vehicle and wheel assembly 3. In an embodiment, imaging device 64 comprises an infrared imaging device, which can acquire image data that computer system 20 can process to evaluate for the presence of worn bearings, stuck brakes, flat spots, and/or the like. In a further embodiment, a pair of imaging devices 64 can be implemented, one of which captures infrared-based image data and another that captures visible light-based image data. In this case, computer system 20 can fuse the two types of image data to evaluate the rail vehicle/wheel assembly 3. To this extent, computer system 20 can implement a process shown and described in co-pending U.S. patent application Ser. Nos. 12/603,958 and 11/748,714, both of which are incorporated by reference, to evaluate one or more components of the rail vehicle.

Furthermore, computer system 20 can combine analysis of the acoustic data with analysis of the image data. In this case, computer system 20 can use the image data to provide independent confirmation of the presence of a condition indicated by the acoustic data, provide additional data on the nature of the condition (e.g., when the acoustic data is sufficient to detect a flaw, but not distinguish between multiple possible flaws), and/or the like. Additionally, computer system 20 can use the image data and acoustic data to identify other types of conditions that may be present on a rail vehicle, such as a hydrogen flame present at a leaking location, which will have both an identifiable acoustic signature and infrared image. In any event, in addition to evaluating one or more rotating components of the rail vehicle, computer system 20 can use the image data to calculate a speed of the rail vehicle, acquire identification information from markings located on the rail vehicle, distinguish one rail vehicle from another, count axles, and/or the like.

Attribute component 12B also is shown including an accelerometer 66, which can be configured to acquire vibration data during the passage of the rail vehicles. Computer system 20 can evaluate the vibration data in conjunction with the acoustic data to evaluate a condition of the bearings. In this case, use of both vibration data and acoustic data by computer system 20 can reduce a total number of false positives and negatives versus using only one type of data.

For implementations of system 10 (FIG. 1), such as the evaluation of rotating components of rail vehicles described herein, computer system 20 can calculate the speed of the moving target object and use the speed to adjust one or more evaluation actions. Computer system 20 can calculate the speed using evaluation data acquired by one or more of the components of acquisition subsystem 12 (FIG. 1). For example, wheel sensors 62A, 62B can acquire sufficient data to enable computer system 20 to determine the speed of a passing rail wheel. In an embodiment, a wheel sensor 62A, 62B includes two wheel detectors a known distance apart (e.g., less than a circumference of a smallest possible wheel). Computer system 20 can use the distance and time difference between the triggering of the two wheel detectors to calculate the speed of the rail vehicle. Similarly, computer system 20 can determine a speed of the rail vehicle by analyzing the acoustic data (e.g., identifying the time difference between peaks in the acoustic data corresponding to multiple wheels with known wheel spacings) and/or image data (e.g., change of feature location in images captured a known time apart) acquired from the passing rail vehicle. Further, system 10 can include one or more sensing components, such as a millimeter-wave sensor (e.g., radar gun), to acquire the speed of the rail vehicle directly.

In various implementations, one or more acoustic sensors, such as acoustic sensor 14C, can be configured to acquire acoustic data for vehicles of varying distances from the acoustic sensor 14C. To this extent, implementations 10A, 10B can be configured to evaluate rotating components of rail vehicles moving along multiple tracks crossing the target area of acoustic sensor 14C. To this extent, system 10 can include one or more sensing components to acquire distance data, and computer system 20 can adjust one or more evaluation actions based on the distance. For example, each track over which rail vehicles can be evaluated by acoustic sensor 14C can include wheel sensors 62A, 62B. Depending on the wheel sensors 62A, 62B that trigger the system, computer system 20 can determine the distance corresponding to the track along which a rail vehicle is moving.

In another embodiment, computer system 20 can determine the track or location of interest by registering average signal envelopes of, for example, the passing rail wheels. In particular, while each individual passing rail wheel will have a unique acoustic signature, general characteristics of the acoustic signatures averaged across several passing rail wheels will appear very similar, with certain parameters (e.g., maximum signal amplitude) varying with distance from the acoustic sensor(s) 14C. Computer system 20 can determine the variance and automatically register the track of interest.

The transmission of sound can be affected by a number of environmental factors. To this extent, the ambient component 12C (FIG. 1) of implementation 10B can include one or more sensing devices 68 configured to acquire ambient data on the surrounding environment. The environmental factors that most directly affect the transmission of sound include temperature and wind speed. In an embodiment, sensing device 68 comprises a thermometer for acquiring temperature data and an anemometer for measuring wind direction/speed. However, other environmental factors, such as rain, may indirectly affect the transmission of sound or introduce additional noise. To this extent, sensing device can comprise, for example, a hygrometer for acquiring humidity data, a precipitation sensor, a barometer for measuring atmospheric pressure, a light sensor for measuring the lighting conditions, a visibility sensor for measuring visibility, and/or the like. Additionally, imaging device 64 can be configured to acquire image data, which computer system 20 processes to determine a lighting condition and/or visibility as shown and described in U.S. Pat. No. 7,602,937, which is incorporated herein by reference. Based on a lighting condition and/or presence of a rail vehicle, computer system 20 can be configured to operate one or more artificial light sources, which can improve the quality of visible light-based image data.

Computer system 20 can use the ambient data and/or attribute data to adjust one or more aspects of the evaluation of the various components. For example, when a single implementation 10B is used to monitor multiple tracks, computer system 20 can adjust processing of the acoustic data based on the stand-off distance. In particular, the stand-off distance can affect the transmission of the sound, thereby altering one or more attributes of the original sound waves, such as signal amplitude, broadening or fuzzing of details, and/or the like. As a result, computer system 20 can adjust one or more of the noise filter(s), the spectral area of interest, the sub-bands within the spectral area of interest, and/or the evaluation of the statistical data when determining whether the acoustic data matches the set of condition criteria for a condition based on the stand-off distance. For example, computer system 20 can multiply all acoustic amplitudes in the acoustic data using a formula:

$$(\text{distance to target}/\text{normalizing distance})^2$$

In a more particular example, computer system 20 can utilize algorithms configured for detecting condition(s) on a vehicle twelve feet away (the normalizing distance). For a vehicle detected as being twenty-four feet away, computer system 20 can multiply the acoustic amplitudes by $(24/12)^2=4$.

Additionally, computer system 20 can adjust the evaluation processing based on a speed of the rail vehicle. For example, computer system 20 can adjust the evaluation algorithm to account for the difference in acoustic amplitude between a fast moving rail vehicle and a slower moving rail vehicle, which can alter expected amplitude ratios and other sound characteristics of the acoustic signals of interest. In particular, as the rail vehicle moves faster, the sounds generated by the rail vehicle will be louder. To this extent, computer system 20 can adjust one or more of the noise filter(s), the spectral area of interest, the sub-bands within the spectral area of interest, and/or the evaluation of the statistical data when determining whether the acoustic data matches the set of condition criteria for a condition based on the speed of the rail vehicle. For example, computer system 20 can multiply all acoustic amplitudes in the acoustic data using a formula:

$$\text{normalizing speed}^2/\text{speed of target}^2$$

In a more particular example, computer system 20 can utilize algorithms configured for detecting condition(s) on a vehicle traveling at twenty miles per hour (the normalizing speed). For a vehicle detected as traveling at forty miles per hour, computer system 20 can multiply the acoustic amplitudes by $20^2/40^2=400/1600=\frac{1}{4}$.

Furthermore, computer system 20 can adjust the evaluation processing based on environmental conditions, such as the temperature, wind direction/speed, atmospheric pressure, precipitation, and/or the like, which can affect an amount of background noise and/or sound propagation. For example, computer system 20 can adjust one or more of the noise filter(s), e.g., by adding noise filter(s) specifically targeted to remove noise due to rain, wind, or the like, adjust more sensitive parameters of the sound identification algorithms to account for changes in sound transmission, and/or the like based on the environmental conditions. For example, while the speed of sound over all temperatures and pressures is roughly the same, sounds are selectively attenuated by frequency based on the actual density of a gas as the sound passes through that gas in a known manner. Since temperature and pressure affect the density of the gas in a known manner, computer system 20 can adjust the frequency bands of the received sounds based on the temperature and/or pressure to normalize the frequencies of the sounds received to a desired density.

Figure 9:
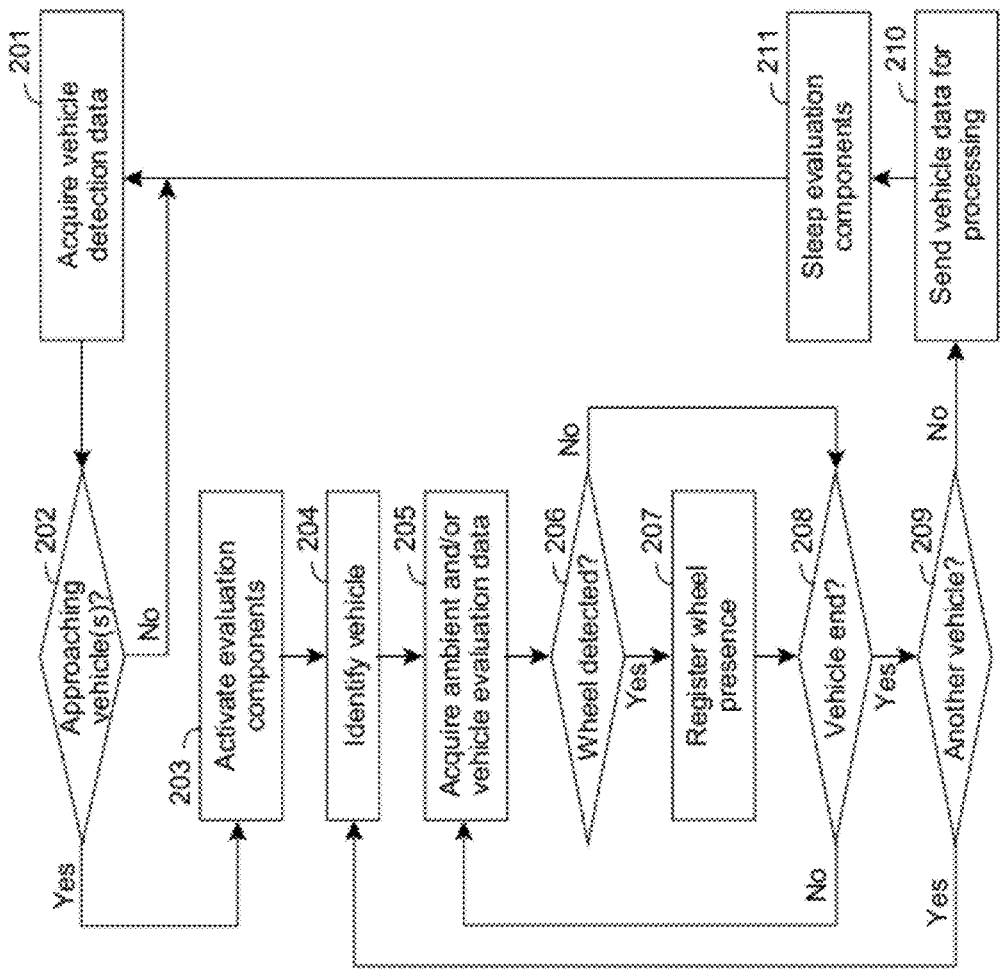
FIG. 9 shows an illustrative process for acquiring component data for evaluating rotating component(s) of a series of vehicles according to an embodiment.

FIG. 9 shows an illustrative process for acquiring component data 40 (FIG. 1) for evaluating rotating component(s) of a series of vehicles according to an embodiment, which can be implemented by system 10 (FIG. 1). The process shown in FIG. 9 is further described with reference to evaluating rotating component(s), in particular the bearings, of a series of rail vehicles. To this extent, the process can be implemented by implementation 10A (FIG. 7) or implementation 10B (FIG. 8).

Referring to FIGS. 7-9, in action 201, computer system 20 obtains vehicle detection data from one or more detection components. For example, the vehicle detection data can be acquired by an electronic vehicle identifier, such as RFID tag reader 60, a physical rail vehicle detector, such as wheel sensors 62A, 62B, and/or the like. It is understood that use of both the vehicle identifier and vehicle detector is not necessary. However, use of a physical rail vehicle detector is less likely to fail (e.g., due to an inoperable/removed RFID tag), while the vehicle identifier can provide additional details (e.g., unique train/rail vehicle identifier, history, routing and manifests, and/or the like), which can enable computer system 20 to implement additional functionality by using the additional data.

In an embodiment, a lower power detection component is used for the initial detection of approaching rail vehicle(s). In this case, RFID tag reader 60 and wheel sensors 62A, 62B can be deactivated along with other components. For example, the detection component can comprise an acoustic pre-trigger component, which can detect an approaching rail vehicle and signal the various components of acquisition subsystem 12 to activate.

The acoustic pre-trigger component can comprise a low-power acoustic sensor, which is configured to identify a set of target sounds that can be readily discriminated from background noise. An illustrative solution for detecting an event with an acoustic sensor is shown and described in U.S. Pat. No. 7,355,508, which is incorporated herein by reference. In particular, the acoustic pre-trigger component can be configured to identify the sound of an approaching locomotive. Locomotives have powerful, very characteristic acoustic signatures from the immensely powerful engines they use to pull thousands of tons of cars and freight, and these engines have characteristic emissions in acoustic bands that few other sources emit. By selecting low-power hardware bandpass filters and using very low-power microcontrollers (e.g., a microcontroller selected from the Texas Instruments MSP-430 line) to perform acoustic processing, such as rising peak level determinations, a very low power acoustic sensor can be utilized to operate as a pre-trigger to reliably detect the approach of a train and activate other components as described herein. In this case, the entire system 10 (FIG. 1) can draw approximately a few milliwatts of power for most of the time period of its operation (e.g., when no vehicles are approaching/being evaluated). Furthermore, such a pre-trigger component can be self-powered and wireless, e.g., by using an approach similar to that shown and described in U.S. patent application Ser. No. 12/493,789, which is incorporated herein by reference.

In action 202, computer system 20 determines whether the vehicle detection data indicates one or more approaching vehicles. If not, the process returns to action 201. However, if a set of vehicles are approaching, in action 203, computer system 20 activates a set of evaluation components. The set of evaluation components includes one or more acoustic sensors 14A-14E, and can include additional sensing devices, such as imaging (e.g., visible and/or infrared) device(s) 64, locally installed wheel sensors 62A, 62B, accelerometer 66, ambient sensing device(s) 68, chemical sensor(s), and/or the like. In action 204, computer system 20 can generate and/or store an identification of the next vehicle that will pass an evaluation area. For example, computer system 20 can use identification information acquired from an RFID tag and/or generate a locally unique identifier for the rail vehicle. Additionally, once acquired, computer system 20 can use identification information imaged from a surface of the vehicle.

In action 205, acquisition subsystem 12 acquires ambient and/or evaluation data as the vehicle moves through an evaluation area. The evaluation data includes acoustic data acquired by one or more acoustic sensors 14A-14E, and can include additional types of data, such as attribute data corresponding to the vehicle and/or one or more of its components, which can be acquired by one or more other types of sensing components of attribute component 12B as described herein. The ambient data can include any type of data on the ambient operating environment, which can be acquired by one or more types of sensing components of ambient component 12C as described herein.

In action 206, a wheel detection device, such as wheel sensor 62B, will identify the presence of a passing wheel. In an embodiment, the wheel detection device is configured such that the wheel is detected when the rotating component(s) being evaluated (e.g., the bearings) are within or nearly within the target area of the acoustic sensor(s) 14A-14E. In response to detecting a wheel, in action 207, the wheel detection device registers the wheel presence. For example, the wheel detection device can place a timing signal into the data stream of a synchronization data channel. The data stream can comprise, for example, an additional acoustic channel recorded in parallel with the main acoustic data channel(s) of acoustic sensor(s) 14A-14E. Various solutions can be implemented to determine when the wheel has traveled sufficiently such that the rotating component(s) being evaluated are outside of the target area. For example, a second wheel sensor 62B can place a second signal into the data stream, attribute data, such as the speed of the rail vehicle or timing between two consecutive wheel detection signals, and/or the like, can be utilized by computer system 20. Regardless, the wheel detection signal(s) will be inherently synchronized with the streaming acoustic data corresponding to the rotating component(s) being evaluated. As a result, computer system 20 can use the wheel detection signals to identify the acoustic data acquired by acoustic sensor(s) 14A-14E that corresponds to a time period during which a particular wheel moved through the target area. Computer system 20 can process only the identified acoustic data to match sounds of interest that correspond to the particular wheel.

In action 208, computer system 20 determines whether the end of a rail vehicle has been detected. For example, computer system 20 can determine that the rail vehicle has ended when a new rail vehicle is detected and/or a rail vehicle end by the detection component(s). If the end of the rail vehicle has not been detected, computer system 20 returns to action 205 and continues to acquire evaluation data. However, if the end of the rail vehicle is detected, in action 209, computer system 20 determines whether another rail vehicle is present. If another rail vehicle is present, computer system 20 returns to action 204 and identifies the next rail vehicle. In an embodiment, computer system 20 implements a process shown and described in co-pending U.S. patent application Ser. Nos.

12/043,357 and 12/171,438, both of which are incorporated by reference, to identify the start/end of various rail vehicles and consists.

Once evaluation and/or attribute data has been acquired for all rail vehicles, in action 210, a local device of computer system 20 can provide the vehicle data, including the component data 40, for evaluation of the rotating component(s) of the vehicle by remotely located device(s) of computer system 20 via, for example, a wireless communications link 54. However, it is understood that some or all of the processing can be implemented by a local device of computer system 20. In an embodiment a local device of computer system 20 implements some pre-processing to identify select segments of the vehicle data of interest. The local device can provide only these segments of interest for evaluation at a remote device of computer system 20, thereby reducing the amount of data required for transmission while continuing to require a reduced amount of processing on site. Regardless, in action 211, computer system 20 can deactivate (e.g., sleep) the set of evaluation components, and return to action 201 until another rail vehicle is detected.

It is understood that the process of FIG. 9 is only illustrative, and numerous variations can be implemented under the invention. For example, depending on a capacity of a local device of computer system 20, some or all of the vehicle data can be evaluated locally as it is acquired. Similarly, computer system 20 can transmit acquired vehicle data while continuing to acquire vehicle data for additional rail vehicles.

Figure 10:
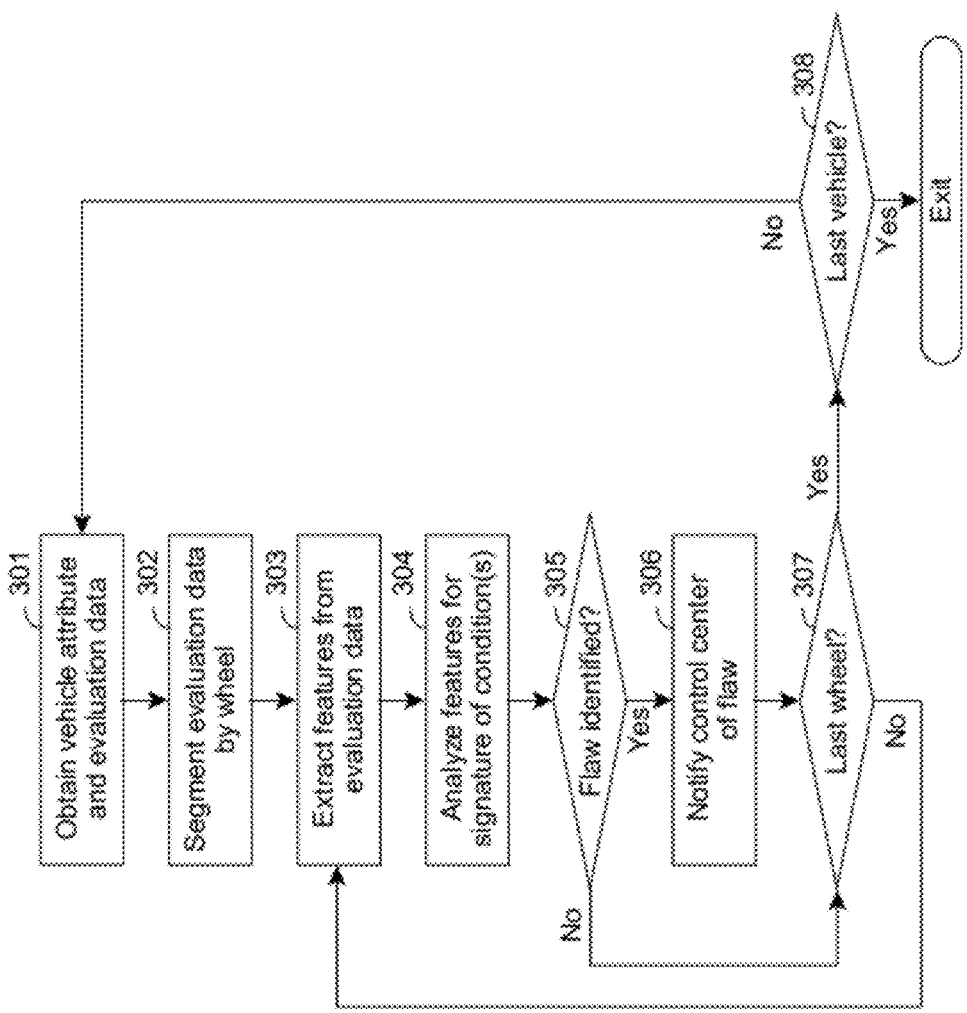
FIG. 10 shows an illustrative process for evaluating rotating component(s) of a series of vehicles according to an embodiment.

FIG. 10 shows an illustrative process for evaluating rotating component(s) of a series of vehicles according to an embodiment, which can be implemented by system 10 (FIG. 1). The process shown in FIG. 10 is further described with reference to evaluating rotating component(s), in particular the bearings, of the wheels of a series of rail vehicles. To this extent, the process can be implemented by implementation 10A (FIG. 7) or implementation 10B (FIG. 8).

Referring to FIGS. 1 and 10, in action 301, computer system 20 obtains vehicle attribute and evaluation data for a vehicle in the series of vehicles and the corresponding rotating component(s) thereof. For example, computer system 20 can acquire the data using the process shown and described in FIG. 1, and a computing device of computer system 20 can obtain the data as shown and described in action 210 of FIG. 9. However, it is understood that all processing can be implemented by a local device of computer system 20. In either case, the evaluation processing can be performed after all the data for a series of rail vehicles is acquired or while data for rail vehicles is continuing to be acquired by computer system 20.

In action 302, computer system 20 segments the evaluation data by wheel. For example, computer system 20 can use wheel detection signal(s) placed in a data stream of a synchronization data channel as described herein to identify the acoustic data corresponding to each wheel. Additionally, when other types of data are included, computer system 20 can identify each wheel using any solution, e.g., by synchronizing the data with the acoustic data, processing the data to identify each new wheel (e.g., using image processing of image data) and/or the like.

In action 303, computer system 20 extracts various features from the evaluation data for a wheel. For example, computer system 20 can process the acoustic data using the process shown and described herein with reference to FIG. 3 to extract features/statistics such as, for example, minima and maxima, averages across some number of points of data, variance across the sample, root mean square (RMS), kurtosis, and/or the like. As described herein, computer system 20 can adjust the processing based on one or more vehicle attributes (e.g., vehicle speed, distance), ambient conditions (e.g., temperature, wind speed/direction), and/or the like. Similarly, computer system 20 can process other types of evaluation data, if acquired, to extract one or more features/statistics. For example, computer system 20 can process image data corresponding to the wheel as described herein. Additionally, computer system 20 can process vibration data corresponding to the wheel. For example, computer system 20 can extract similar features/statistics from the vibration data as described in conjunction with the acoustic data.

In action 304, computer system 20 analyzes the various features to determine whether the signature of one or more condition(s) of the rotating component are present. For example, computer system 20 can process the acoustic data using the process shown and described herein with reference to FIG. 3 to determine whether the acoustic data indicates the presence of one or more conditions being evaluated for the rotating component. As described herein, computer system 20 can adjust the processing based on one or more vehicle attributes (e.g., vehicle speed, distance), ambient conditions (e.g., temperature, wind speed/direction), and/or the like. Similarly, computer system 20 can process other types of evaluation data, if acquired, to determine whether one or more conditions being evaluated are present. For example, computer system 20 can process image data corresponding to the wheel as described herein. Additionally, computer system 20 can process vibration data corresponding to the wheel, e.g., by using a set of vibration condition criteria corresponding to one or more conditions capable of being evaluated for the rotating component using the vibration data.

In action 305, computer system 20 can determine whether a flaw was identified for the rotating component(s) of the corresponding wheel. In an embodiment, computer system 20 fuses the results obtained from separately evaluating the flaw using multiple types of evaluation data to determine whether a flaw is present, or whether a confounding condition was identified using any solution. For example, computer system 20 can identify a flaw in the wheel bearings only if both the image data and the acoustic data indicate the flaw.

If a flaw is detected, in action 306, computer system 20 notifies a control center of the flaw. The control center can comprise, for example, a control center located at a classification yard at which system 10 (FIG. 1) is deployed or towards which the rail vehicle is traveling. Alternatively, the control center can comprise a local display to maintenance personnel, a central maintenance database, the owner or operator of the rail vehicle/train, and/or the like. Computer system 20 can communicate the notification using any communications solution.

Regardless of whether a flaw is detected, in action 307, computer system 20 determines whether another wheel of a vehicle requires evaluation. If so, computer system 20 returns to action 303 and evaluates the wheel. If not, in action 308, computer system 20 determines whether the rotating component(s) of the last vehicle in the series of vehicles has been evaluated. If not, computer system 20 returns to process 301 to obtain the data for the next vehicle in the series of vehicles. Once the rotating component(s) of all of the vehicles in the series of vehicles have been evaluated, computer system 20 exits the process.

While shown and described with reference to the evaluation of rotating components of rail vehicles, it is understood that embodiments of the invention are not limited to this application. For example, an embodiment of the invention can be implemented to inspect other types of vehicles, such as commercial trucks and buses, smaller private vehicles, and even vehicles such as jet aircraft. To this extent, an embodiment of system 10 (FIG. 1) can be implemented at a vehicle weigh station or other vehicle inspection venue, which would enable enforcement officials to evaluate the vehicles of one or more flaws, such as those indicative of bearing failure. The evaluation can be used for pre-screening a vehicle for additional inspection. In this manner, vehicles showing significant flaws that may affect the safety of continued operation of the vehicle can be preferentially inspected and, if necessary, removed from service.

Figure 11:
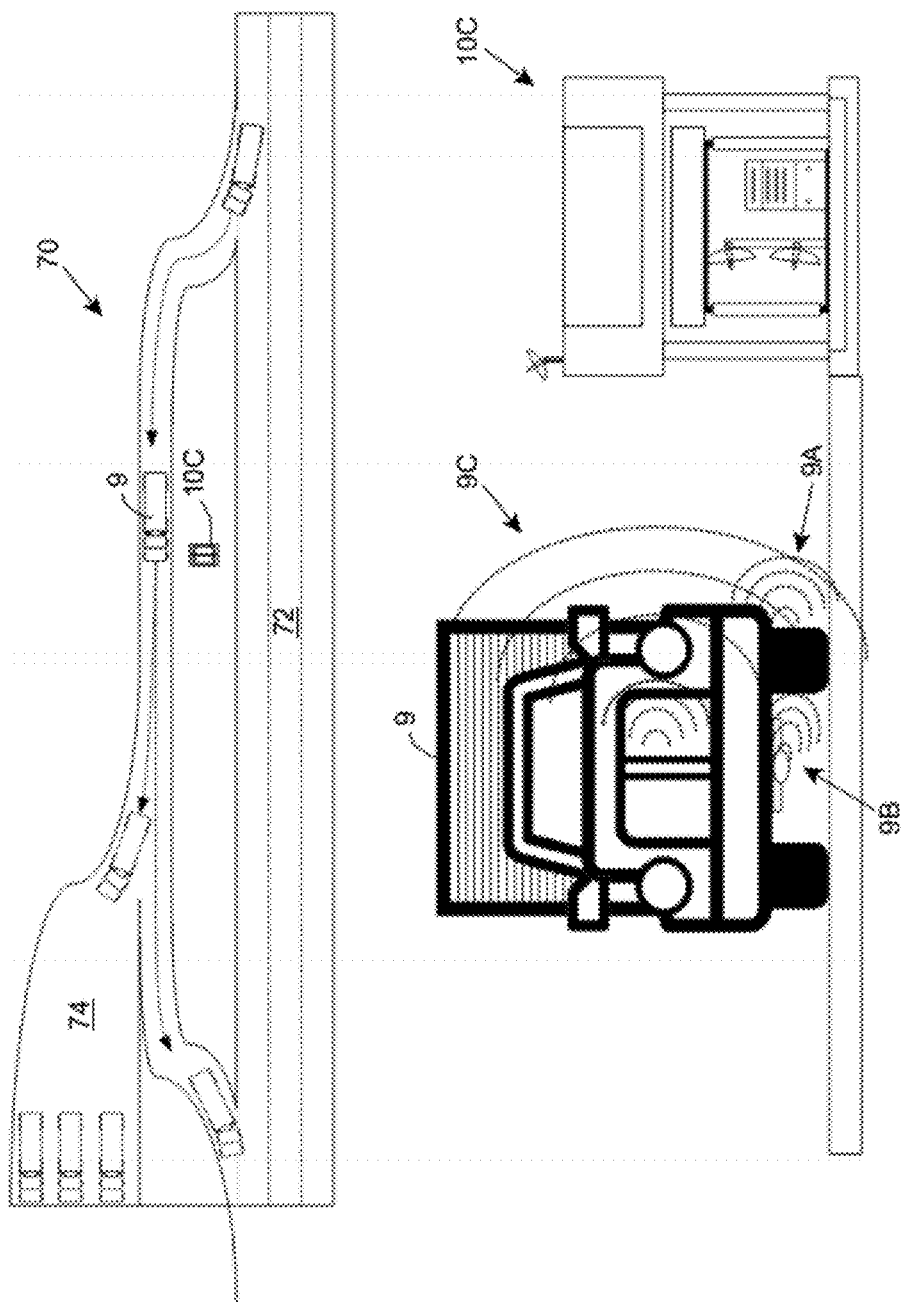
FIG. 11 shows top and side views of an illustrative implementation of the system of FIG. 1 for evaluating a set of rotating components of commercial vehicles according to an embodiment.

FIG. 11 shows top and side views of an illustrative implementation 10C of system 10 for evaluating a set of rotating components of commercial vehicles according to an embodiment. In particular, implementation 10C is located at an inspection area 70 located off of a highway 72. Trucks, such as truck 9, traveling on the highway 72 are required to pull into inspection area 70 for inspection. While most trucks readily pass inspection, such a requirement can cause considerable delay for all trucks as they wait to be inspected.

However, as described herein, implementation 10C can evaluate one or more rotating components of the trucks 9 using acoustic data as they enter the inspection area 70 to determine the presence of one or more flaws in the rotating component(s). For example, implementation 10C can be configured to evaluate acoustic signals generated from one or more of: the wheel area 9A, including the wheel, bearings of the wheel, portions of the suspension, and/or brakes; the transmission area 9B, which contains a number of moving components for gearing that can develop audible flaws; and the engine 9C, which also includes a number of operating components and subsystems whose associated sounds may provide useful diagnostic information. Similar to evaluation of rotating components of rail vehicles described herein, there are a number of approaches, ranging from theoretical modeling of systems to gathering of empirical data on many operating trucks, which can be utilized to configure computer system 20 to be capable of determining particular acoustic signatures of target flaws.

Regardless, when a flaw is potentially present, the truck can be routed to an inspection lot 74 for further inspection. Otherwise, the truck can be allowed to return to the highway 72. Since only a small fraction of vehicles can normally be inspected, implementation 10C can enable the inspection efforts to focus on vehicles that have or are likely to have defects in need of addressing, and also allow vehicles with no noticeable defects to proceed onward with a relatively small delay as compared to current inspection areas.

In an embodiment, system 10 (FIG. 1) can be implemented as part of a preventive maintenance system for a fleet of commercial vehicles. For example, one or more implementations of system 10 can be located in one or more locations that a vehicle will periodically pass during normal operation, such as a rail vehicle (e.g., a station for a passenger rail vehicle), truck (e.g., at a warehouse), bus (e.g., at a bus station). In this case, the evaluation data acquired each pass can be stored and analyzed over time to generate a trend history for the vehicle and/or trending patterns for a fleet of vehicles.

An entity can use the trending analysis to implement a predictive health maintenance (PHM) program for the fleet of vehicles. For example, since the wear on bearings and other rotating components can be detected very early using acoustic data analysis as described herein, and in settings which enable relatively frequent examinations of the same vehicle, hard data can be acquired on how long it takes these rotating components to reach a state that requires replacement. As a result, the PHM program will be able to determine, within a fairly narrow range, when replacement of a rotating component will be needed and schedule replacement so as to minimally disrupt traffic and maximally use all components of the vehicles while maintaining safe performance throughout the transport network. Additionally, any variation in trending also can identify problem areas in the transport infrastructure. For instance, if vehicles traveling over a particular route show swifter degradation than those traveling other routes, this may be an indication that maintenance is needed on the infrastructure (e.g., rails or roads) in that location.

Additionally, it is understood that embodiments of the invention are not limited to applications involving the evaluation of rotating components of moving objects. To this extent, an embodiment of system 10 can be implemented to evaluate the rotating component(s) of one or more of many forms of machinery, ranging from motors to manufacturing systems to power generation turbines, which are fixed but contain many moving components that can generate recognizable acoustic signatures both when operating normally and when in various failure modes. Further, an embodiment of system 10 can be used to monitor an area, e.g., to characterize ambient noises from vehicles, construction sites, and/or the like, for monitoring the area for any unusual activity.

Figure 12:
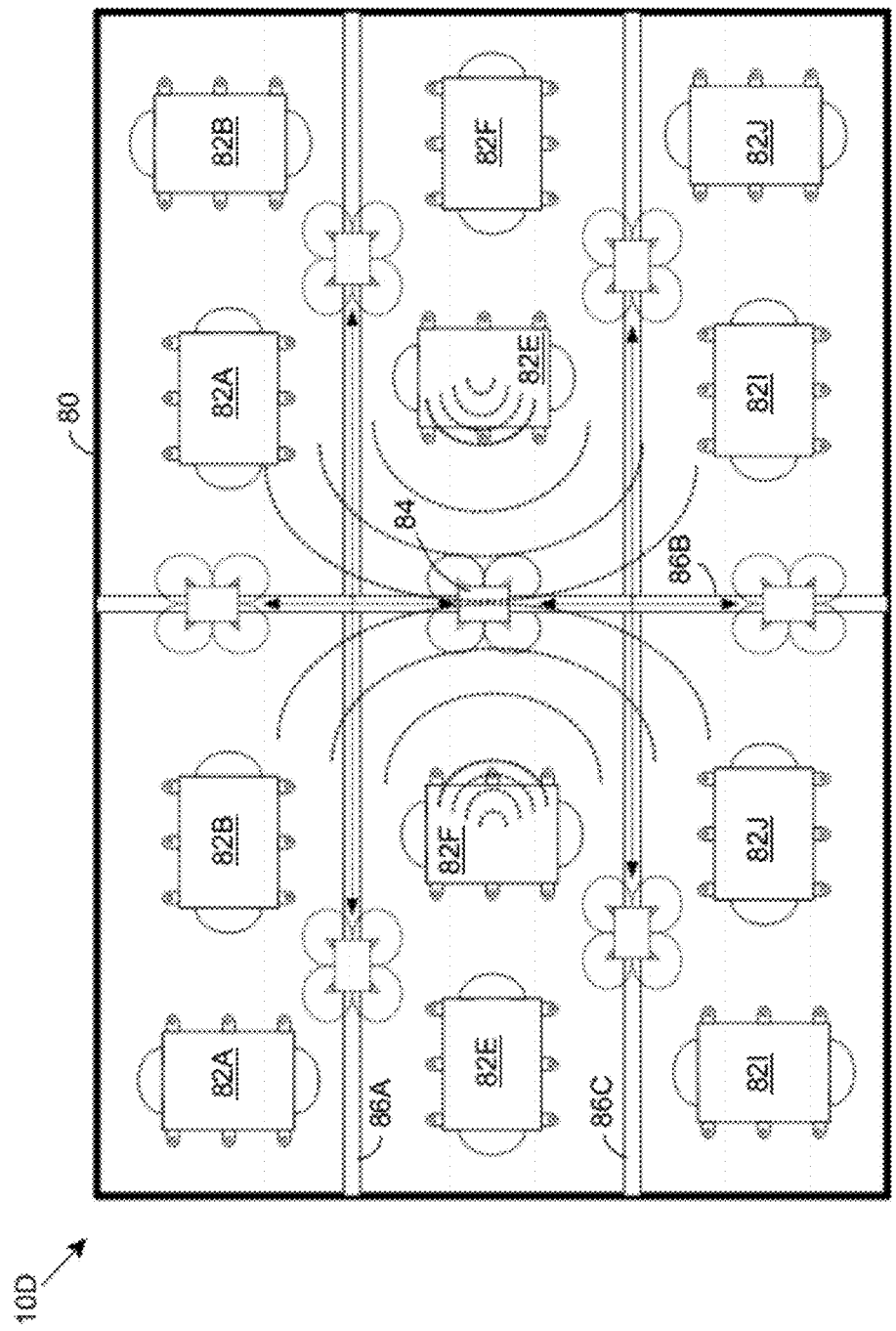
FIG. 12 shows an illustrative implementation of the system of FIG. 1 for evaluating a set of rotating components of stationary machines according to an embodiment.

FIG. 12 shows an illustrative implementation 10D of system 10 for evaluating a set of rotating components of stationary machines according to an embodiment. In implementation 10D, an installation 80 includes a number of stationary machines of interest, such as machines 82A-82L, which can be monitored/evaluated using an acoustical monitoring assembly 84. Installation 80 can comprise, for example, a floor of a production plant or other type of manufacturing facility that includes various machines 82A-82L used in a manufacturing process. One or more of machines 82A-82L can be substantially identical or machines 82A-82L can include machines that vary significantly by size, shape, mode of operation, and/or the like, so long as each machine 82A-82L to be monitored using monitoring assembly 84 generates acoustic signal(s) that can be acquired by one or more directional acoustic sensors on monitoring assembly 84 and characterized and used for evaluation by a computer system and/or expert listener.

In implementation 10D, monitoring assembly 84 can be configured to be moved and positioned in any of various locations to monitor a machine 82A-82L. To this extent, monitoring assembly 84 includes a motive assembly, which is configured to move the monitoring assembly 84 along a set of rails 86A-86C, such that monitoring assembly 84 can be placed to monitor any of the machines 82A-82L. Rails 86A-86C can be mounted overhead or along a floor on which target machines 82A-82L are located. Additionally, one more directional acoustic sensors on monitoring assembly 84 can be configured to be selectively moved to place a set of rotating components of a target machine 82A-82L within a target area of the acoustic sensor. However, it is understood that this implementation 10D is only illustrative. For example, the acoustic sensor(s) can be located at a fixed location and/or a target area of the acoustic sensor(s) can be moved to adjust the area of focus. Additionally, monitoring assembly 84 can be mounted on a moving platform (e.g., an overhead platform), a crane, or the like, which passes over the location(s) of operating machine(s) to acquire acoustic data.

While the various illustrative implementations described herein have been shown as being permanently emplaced in a location, it is understood that the various components of acquisition subsystem 12 (FIG. 1) and a computer system 20 (FIG. 1) can be temporarily located at a particular location (e.g., to perform an unannounced evaluation). The temporary emplacement can be implemented using adjustable supports with the acoustic sensor(s) installed thereon. In such a design, lightweight components, foldable or otherwise easily transported parabolic microphones, temporary shelters, and so on, can be used to set up the temporary emplacement.

While shown and described herein as a method and system for evaluating rotating component(s) using acoustic data, it is understood that aspects of the invention further provide various alternative embodiments. For example, in one embodiment, the invention provides a computer program fixed in at least one computer-readable medium, which when executed, enables a computer system to evaluate rotating component(s) using acoustic data. To this extent, the computer-readable medium includes program code, such as evaluation program 30 (FIG. 1), which implements some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as evaluation program 30 (FIG. 1), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for evaluating rotating component(s) using acoustic data. In this case, an acquisition subsystem, such as acquisition subsystem 12 (FIG. 1), and a computer system, such as computer system 20 (FIG. 1), can be obtained (e.g., created, maintained, made available, etc.) and one or more components for performing a process described herein can be obtained (e.g., created, purchased, used, modified, etc.) and deployed to the system. To this extent, the deployment can comprise one or more of: (1) installing program code on a computing device; (2) adding one or more computing and/or I/O devices to the system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
    an acoustic sensor configured to acquire acoustic data corresponding to a rotating component of a machine during operation of the machine within a target area of the acoustic sensor, wherein the acoustic sensor is physically separated from the machine, and wherein the acoustic sensor is configured to enhance acoustic signals in a range of frequencies corresponding to at least one evaluated condition of the rotating component and enhance the acoustic signals received from a directional area narrowly focused on the rotating component; and
    a computer system including at least one computing device configured to evaluate the rotating component by:
        determining whether any one of the at least one evaluated condition is present in the rotating component based on the acoustic data corresponding to the rotating component.

2. The system of claim 1, wherein the determining includes extracting a set of features from the acoustic data corresponding to the rotating component and analyzing the set of features for at least one condition feature associated with the at least one evaluated condition.

3. The system of claim 2, wherein the evaluation further includes removing background noise from the acoustic data prior to the extracting using a noise model corresponding to a deployment location of the acoustic sensor.

4. The system of claim 2, wherein the extracting includes generating a set of statistics based on at least one of: acoustic data corresponding to the range of frequencies or a plurality of sub-bands of the range of frequencies.

5. A system comprising:
    an acoustic sensor configured to acquire acoustic data corresponding to a rotating component of a machine during operation of the machine, wherein the acoustic sensor is configured to enhance acoustic signals in a range of frequencies corresponding to at least one evaluated condition of the rotating component and enhance the acoustic signals received from a directional area narrowly focused on the rotating component; and
    a computer system including at least one computing device configured to evaluate the rotating component by:
        determining whether any one of the at least one evaluated condition is present in the rotating component based on the acoustic data corresponding to the rotating component, wherein the determining includes:
            extracting a set of features from the acoustic data corresponding to the rotating component; and
            analyzing the set of features for at least one condition feature associated with the at least one evaluated condition, wherein the set of features are determined using an exemplar acoustic sensor different from the acoustic sensor; and
        adjusting the acoustic data using a correction function corresponding to a difference between a response parameter of the acoustic sensor and a response parameter of the exemplar acoustic sensor over the range of frequencies prior to the extracting.

6. The system of claim 1, wherein the acoustic sensor comprises a parabolic microphone having a main directional area within which the rotating component is located during a time period that the acoustic data corresponding to the rotating component is acquired.

7. The system of claim 6, wherein the main directional area is configured such that the rotating component is the only sound source within the main directional area during the time period.

8. A system comprising:
    an acoustic sensor configured to acquire acoustic data corresponding to a rotating component of a machine during operation of the machine, wherein the acoustic sensor is configured to enhance acoustic signals in a range of frequencies corresponding to at least one evaluated condition of the rotating component and enhance the acoustic signals received from a directional area narrowly focused on the rotating component;

at least one attribute sensing device configured to acquire attribute data corresponding to at least one of the rotating component or the machine; and a computer system including at least one computing device configured to evaluate the rotating component by:
- determining whether any one of the at least one evaluated condition is present in the rotating component based on the acoustic data corresponding to the rotating component; and
- associating the attribute data corresponding to the rotating component with the result of the determining.

9. A system comprising:

an acoustic sensor configured to acquire acoustic data corresponding to a rotating component of a machine during operation of the machine, wherein the acoustic sensor is configured to enhance acoustic signals in a range of frequencies corresponding to at least one evaluated condition of the rotating component and enhance the acoustic signals received from a directional area narrowly focused on the rotating component;

at least one ambient sensing device configured to acquire ambient data corresponding to an environment in which the at least one acoustic sensor is operating and a computer system including at least one computing device configured to evaluate the rotating component by:
- determining whether any one of the at least one evaluated condition is present in the rotating component based on the acoustic data corresponding to the rotating component; and
- adjusting at least one aspect of the determining based on the ambient data.

10. The system of claim 9, wherein the ambient data comprises at least one of a temperature, a wind direction, or a wind speed of the environment.

11. A system comprising:

an acoustic sensor configured to acquire acoustic data received from a fixed narrowly focused directional area, wherein the directional area includes a target area through which a rotating component of a vehicle moves during operation of the vehicle;

a second acoustic sensor configured to acquire acoustic data received from a second fixed narrowly focused directional area, wherein the directional area and the second directional area converge at the target area; and a computer system including at least one computing device configured to evaluate the rotating component by:
- obtaining acoustic data corresponding to the rotating component acquired by both the acoustic sensor and the second acoustic sensor as the rotating component moved through the target area; and
- determining whether any one of at least one evaluated condition is present in the rotating component based on the acoustic data corresponding to the rotating component, the determining including: extracting a set of features from the acoustic data corresponding to the rotating component and analyzing the set of features for at least one condition feature associated with the at least one evaluated condition.

12. The system of claim 11, wherein the acoustic sensor is configured such that the target area includes only a single rotating component on the vehicle during a time period that the acoustic data corresponding to the rotating component is acquired.

13. The system of claim 11, further comprising an electronic reader configured to acquire electronic identification data corresponding to the vehicle, and wherein the at least one computing device is further configured to associate the electronic identification data with a result of the evaluation.

14. A system comprising:

an acoustic sensor configured to acquire acoustic data received from a fixed narrowly focused directional area, wherein the directional area includes a target area through which a rotating component of a rail vehicle moves during operation of the rail vehicle, and wherein the acoustic sensor is configured to enhance acoustic signals in a range of frequencies corresponding to at least one evaluated condition of the rotating component and enhance the acoustic signals received from a directional area narrowly focused on the rotating component; and a computer system including at least one computing device configured to evaluate the rotating component by:
- obtaining acoustic data corresponding to the rotating component as the rotating component moved through the target area; determining whether any one of at least one evaluated condition is present in the rotating component based on the acoustic data corresponding to the rotating component, the determining including: extracting a set of features from the acoustic data corresponding to the rotating component and analyzing the set of features for at least one condition feature associated with the at least one evaluated condition.

15. The system of claim 14, wherein the rotating component comprises a railroad wheel bearing.

16. The system of claim 14, further comprising a wheel sensor located adjacent to a rail over which the rail vehicle travels, wherein the wheel sensor is configured to place a timing signal into a data stream of a synchronization data channel, and wherein the obtaining includes identifying the acoustic data acquired by the acoustic sensor that corresponds to the rotating component as the rotating component moved through the target area.

17. The system of claim 14, further comprising an acoustic pre-trigger component configured to generate a signal in response to detecting an approaching set of rail vehicles, wherein the at least one computing device is further configured to activate the acoustic sensor in response to the signal.

18. The system of claim 14, wherein the evaluation further includes calculating a speed of the rail vehicle and adjusting at least one aspect of the extracting or the analyzing based on the speed of the rail vehicle.

19. The system of claim 14, further comprising an imaging device configured to acquire image data corresponding to the rotating component, wherein the evaluation further includes determining whether any one of at least one evaluated condition is present in the rotating component based on the image data and generating a result of the evaluation based on a combination of the results for both determinations.

20. The system of claim 14, further comprising at least one ambient sensing device configured to acquire ambient data corresponding to an environment in which the at least one acoustic sensor is operating, wherein the evaluation further includes adjusting at least one aspect of the determining based on the ambient data.

* * * * *